United States Patent
Yoshimura

(10) Patent No.: US 9,494,685 B2
(45) Date of Patent: Nov. 15, 2016

(54) LIGHT GUIDE MEMBER, OBJECT DETECTION APPARATUS, AND VEHICLE

(71) Applicant: Kenichi Yoshimura, Kanagawa (JP)

(72) Inventor: Kenichi Yoshimura, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 135 days.

(21) Appl. No.: 14/467,199

(22) Filed: Aug. 25, 2014

(65) Prior Publication Data

US 2015/0069223 A1  Mar. 12, 2015

(30) Foreign Application Priority Data

Sep. 6, 2013  (JP) .................................. 2013-184686

(51) Int. Cl.
*G01J 1/04* (2006.01)
*G01S 17/02* (2006.01)
(Continued)

(52) U.S. Cl.
CPC ............ *G01S 17/026* (2013.01); *B60S 1/0833* (2013.01); *B60S 1/0837* (2013.01); *B60S 1/0844* (2013.01); *G01N 21/552* (2013.01); *G02B 6/26* (2013.01); *G01N 21/3554* (2013.01); *G01N 21/43* (2013.01); *G01N 21/4738* (2013.01); *G01N 2021/3155* (2013.01); *G01N 2021/9586* (2013.01); *G01N 2201/064* (2013.01);
(Continued)

(58) Field of Classification Search
CPC .................... B60S 1/0837; G02B 6/26; G01N 21/552
USPC ..................................................... 250/227.14
See application file for complete search history.

(56) References Cited

U.S. PATENT DOCUMENTS 5,556,493 A  9/1996 Teder et al.
5,661,303 A  8/1997 Teder
(Continued)

FOREIGN PATENT DOCUMENTS

DE  4017063 A1  11/1991
DE  10261244 A1  7/2004
(Continued)

OTHER PUBLICATIONS

Jan. 27, 2015 European search report in corresponding European Patent Application No. 14181500.1.

*Primary Examiner* — Thanh Luu
(74) *Attorney, Agent, or Firm* — Cooper & Dunham LLP

(57) ABSTRACT

A light guide member for an object detection apparatus for detecting an object adhered on a light translucent member based on change of quantity of reflection light received from the light translucent member includes a detection face where light exits to the light translucent member and reflection light reflected from the light translucent member enters, the detection face including a detection area where a part of the reflection light to enter the detection unit passes through, and a non-detection area where remaining part of the reflection light not to enter the detection unit passes through; a first intervening member disposed on the detection face attachable to the light translucent member via the first intervening member; and a second intervening member disposed on the detection face attachable to the light translucent member via the second intervening member. The first intervening member has flexibility greater than flexibility of the second intervening member.

17 Claims, 21 Drawing Sheets

(51) Int. Cl.
*B60S 1/08* (2006.01)
*G01N 21/552* (2014.01)
*G02B 6/26* (2006.01)
*G01N 21/3554* (2014.01)
*G01N 21/43* (2006.01)
*G01N 21/47* (2006.01)
*G02B 5/04* (2006.01)
*G01N 21/31* (2006.01)
*G01N 21/958* (2006.01)

(52) U.S. Cl.
CPC ........... *G01N 2201/0626* (2013.01); *G01N 2201/0631* (2013.01); *G01N 2201/0636* (2013.01); *G02B 5/04* (2013.01)

(56) References Cited

U.S. PATENT DOCUMENTS

| | | |
|---|---|---|
| 5,743,991 A | 4/1998 | Teder et al. |
| 5,898,183 A | 4/1999 | Teder |
| 2001/0039990 A1 | 11/2001 | Gold et al. |
| 2006/0076477 A1* | 4/2006 | Ishikawa ............... B60S 1/0822 250/227.25 |
| 2009/0127444 A1 | 5/2009 | Ishikawa |
| 2010/0208060 A1 | 8/2010 | Kobayashi et al. |
| 2011/0001977 A1 | 1/2011 | Goto |

FOREIGN PATENT DOCUMENTS

| | | |
|---|---|---|
| JP | 11-304700 | 11/1999 |
| JP | 2000-131231 | 5/2000 |
| JP | 2000-193588 | 7/2000 |
| JP | 2002-283968 | 10/2002 |
| JP | 2010-210607 | 9/2010 |

* cited by examiner

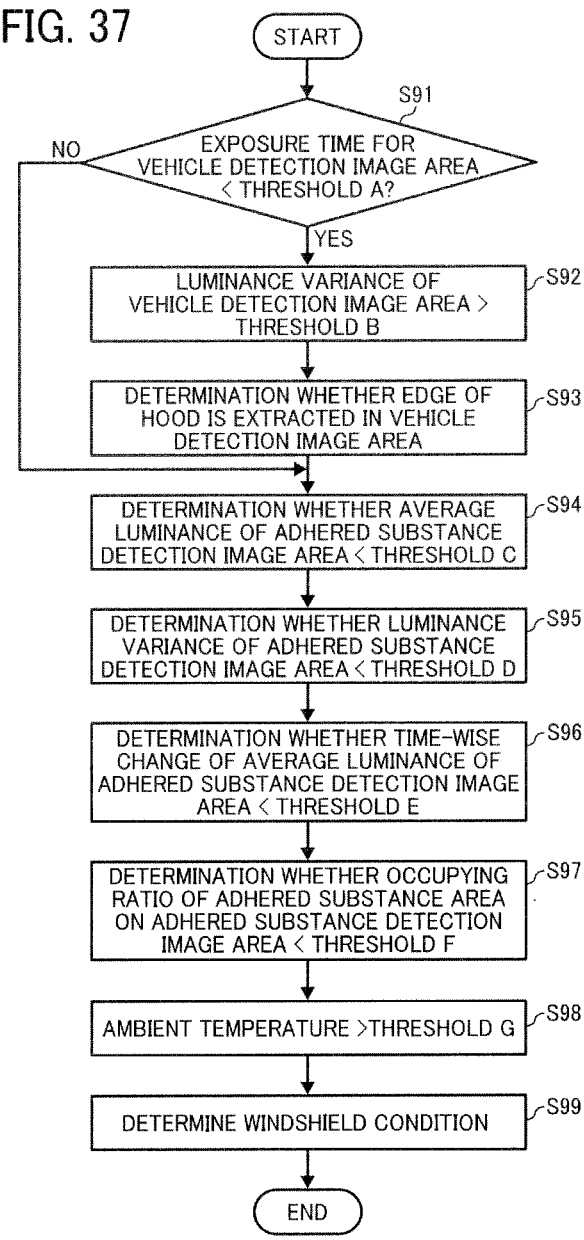

FIG. 38

| DETERMINATION RESULT | DURING DAY | | | | | | |
|---|---|---|---|---|---|---|---|
| | NORMAL | LIGHT RAIN | RAIN | HEAVY RAIN | SPLASH | FOGGING | FREEZING |
| EXPOSURE TIME OF AREA A < THRESHOLD A | NO | NO | NO | NO | NO | NO | NO |
| LUMINANCE DIFFERENCE OF AREA A > THRESHOLD B | YES | YES | YES | NO | NO | NO | NO |
| EDGE OF HOOD OF AREA A (HORIZONTAL EDGE) CAN BE DETECTED | YES | YES | YES | NO | NO | NO | NO |
| AVERAGE LUMINANCE OF AREA B < THRESHOLD C | NO | YES | YES | YES | YES | YES | YES |
| LUMINANCE VARIANCE OF AREA B > THRESHOLD D | NO | NO | YES | YES | NO | NO | NO |
| CHANGE OF AVERAGE LUMINANCE OF AREA B < THRESHOLD E | YES | YES | YES | YES | NO | YES | YES |
| OCCUPYING RATIO OF ADHERED SUBSTANCE AREA OF AREA B < THRESHOLD F | YES | YES | NO | NO | NO | NO | NO |
| AMBIENT TEMPERATURE > THRESHOLD G | YES | YES | YES | YES | YES | YES | NO |

FIG. 39

| DETERMINATION RESULT | NORMAL | NIGHT | | | | | |
|---|---|---|---|---|---|---|---|
| | | LIGHT RAIN | RAIN | HEAVY RAIN | SPLASH | FOGGING | FREEZING |
| EXPOSURE TIME OF AREA A < THRESHOLD A | YES | YES | YES | YES | YES | YES | YES |
| LUMINANCE DIFFERENCE OF AREA A > THRESHOLD B | NOT USED | NOT USED | NOT USED | NOT USED | NOT USED | NOT USED | NOT USED |
| EDGE OF HOOD OF AREA A (HORIZONTAL EDGE) CAN BE DETECTED | NOT USED | NOT USED | NOT USED | NOT USED | NOT USED | NOT USED | NOT USED |
| AVERAGE LUMINANCE OF AREA B < THRESHOLD C | NO | YES | YES | YES | YES | YES | YES |
| LUMINANCE VARIANCE OF AREA B > THRESHOLD D | NO | NO | YES | YES | YES | NO | NO |
| CHANGE OF AVERAGE LUMINANCE OF AREA B < THRESHOLD E | YES | YES | YES | YES | NO | YES | YES |
| OCCUPYING RATIO OF ADHERED SUBSTANCE AREA OF AREA B < THRESHOLD F | YES | YES | NO | NO | NO | NO | NO |
| AMBIENT TEMPERATURE > THRESHOLD G | YES | YES | YES | YES | YES | YES | NO |

FIG. 40

| CONDITION | WIPER CONTROL | DEFROSTER CONTROL |
|---|---|---|
| NORMAL | NOT ACTIVATED | NOT ACTIVATED |
| LIGHT RAIN | ACTIVATED (SLOW SPEED) | NOT ACTIVATED |
| RAIN | ACTIVATED (NORMAL SPEED) | NOT ACTIVATED |
| HEAVY RAIN | ACTIVATED (FAST SPEED) | NOT ACTIVATED |
| SPLASH | ACTIVATED (FAST SPEED) | NOT ACTIVATED |
| FOGGING | ACTIVATED (SLOW SPEED) | ACTIVATED |
| FREEZING | NOT ACTIVATED | ACTIVATED |

LIGHT GUIDE MEMBER, OBJECT DETECTION APPARATUS, AND VEHICLE

This application claims priority pursuant to 35 U.S.C. §119(a) to Japanese Patent Application No. 2013-184686, filed on Sep. 6, 2013 in the Japan Patent Office, the disclosures of which are incorporated by reference herein in their entirety.

BACKGROUND

1. Technical Field

The present invention relates to a light guide member, and an object detection apparatus having the light guide member, and a vehicle.

2. Background Art

Object detection apparatuses for detecting an object (e.g., raindrop) adhered on a surface of a light translucent member (e.g., windshield) composing a vehicle are known.

The object detection apparatus includes, for example, a light source such as a light emitting element that emits light to irradiate an object, and a detection unit such as a light receiving element to receive reflection light reflected from the object and to detect the object based on change of light quantity of the received reflection light.

The object detection apparatus includes, for example, a light guide member made of translucent material, disposed between the light translucent member (e.g., windshield), and the light source and the detection unit to guide light exiting from the light source and reflection light reflected from an object.

As to the object detection apparatus including the light guide member, to avoid false detection of an object, it is required that air bubble does not exist between the light guide member and the light translucent member.

In view of this, when installing the object detection apparatus, adhesive material such as adhesive layer or adhesive sheet may be disposed between the light guide member and the light translucent member to prevent intrusion of air bubble between the light guide member and the light translucent member as disclosed in JP-H11-304700-A and JP-2000-131231-A.

Typically, a windshield attached with the object detection apparatus has a three-dimensional curved face in line with a designed shape of a vehicle.

As to conventional object detection apparatuses, because a shape of the windshield and a shape of contact face of the light guide member are different, when the light guide member is attached to a three-dimensional curved face of the windshield, air bubble may intrude between the adhesive and the windshield and/or between the adhesive and the light guide member.

As to conventional object detection apparatuses, the light guide member is contacted to the windshield, which is a three-dimensional curved face, via adhesive material. To facilitate efficiency of attachment work, the light guide member is fixed to the windshield via an adhesive sheet having higher flexibility.

However, the adhesive sheet having higher flexibility deforms easily. For example, when inertia force effects to the light guide member due to acceleration/deceleration or vibration of a vehicle, the adhesive sheet deforms, with which the relative position of the light guide member with respect to the vehicle may deviate or fluctuate.

If the relative position of the light guide member with respect to the vehicle deviates or fluctuates, the relative position of the light guide member with respect to the windshield, the detection unit, and the light source configuring the object detection apparatus deviates or fluctuates, with which light quantity detected by the detection unit may change or fluctuate.

As to the object detection apparatus, adhered object such as raindrop is detected based on change of light quantity detected by the detection unit. If inertia force effects to the light guide member when an object does not adhere on the windshield, the object detection apparatus may falsely detect that an adhered object exists, with which detection precision deteriorates.

Detection sensitivity of the adhered object can be improved by enlarging a detection area of adhered object. To enlarge detection area of adhered object, an area of the adhesive sheet configuring a contact face contacted to the windshield is required to be greater.

To contact the light guide member to the windshield having the three-dimensional curved face via the adhesive sheet, the adhesive sheet having higher flexibility is required to be used. Therefore, as to the object detection apparatus attachable to the windshield having the three-dimensional curved face via the light guide member, when inertia force effects to the light guide member, detection precision of the adhered object may deteriorate as described above.

SUMMARY

In one aspect of the present invention, a light guide member useable for an object detection apparatus is devised. The object detection apparatus includes a light source unit, and a detection unit for detecting an object adhered on a surface of a light translucent member, configuring a vehicle, based on change of light quantity of reflection light received from the light translucent member when light exiting from the light source unit is reflected from the light translucent member having a face having curvature. The light guide member includes a detection face where the exiting light exits to a rear face of the light translucent member and the reflection light reflected from the light translucent member enters, the detection face including a detection area where a part of the reflection light to enter the detection unit passes through, and a non-detection area where remaining part of the reflection light not to enter the detection unit passes through; a first intervening member disposed on the detection face, a part or entire of the detection area attachable to a rear face of the light translucent member via the first intervening member, and a second intervening member disposed on the detection face, a part or entire of the non-detection area attachable to the rear face of the light translucent member via the second intervening member. The first intervening member has flexibility greater than flexibility of the second intervening member.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 37 is a flowchart showing the steps of a process of determining conditions of a windshield.

FIG. 38 is a table having determination criteria for determining conditions of a windshield;

FIG. 39 is a table having determination criteria for determining conditions of a windshield;

FIG. 40 is an example of table for wiper control and defroster control;

Figure 1:
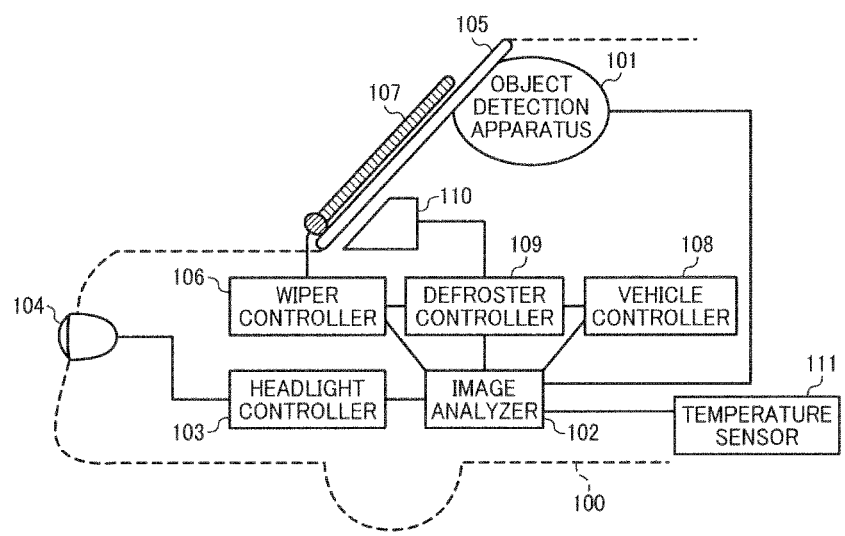
FIG. 1 is a schematic configuration of a vehicle equipped with an object detection apparatus according to an example embodiment.

The accompanying drawings are intended to depict exemplary embodiments of the present invention and should not be interpreted to limit the scope thereof. The accompanying drawings are not to be considered as drawn to scale unless explicitly noted, and identical or similar reference numerals designate identical or similar components throughout the several views.

DETAILED DESCRIPTION

A description is now given of exemplary embodiments of the present invention. It should be noted that although such terms as first, second, etc. may be used herein to describe various elements, components, regions, layers and/or sections, it should be understood that such elements, components, regions, layers and/or sections are not limited thereby because such terms are relative, that is, used only to distinguish one element, component, region, layer or section from another region, layer or section. Thus, for example, a first element, component, region, layer or section discussed below could be termed a second element, component, region, layer or section without departing from the teachings of the present invention.

In addition, it should be noted that the terminology used herein is for the purpose of describing particular embodiments only and is not intended to be limiting of the present invention. Thus, for example, as used herein, the singular forms "a", "an" and "the" are intended to include the plural forms as well, unless the context clearly indicates otherwise. Moreover, the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Furthermore, although in describing views shown in the drawings, specific terminology is employed for the sake of clarity, the present disclosure is not limited to the specific terminology so selected and it is to be understood that each specific element includes all technical equivalents that operate in a similar manner and achieve a similar result. Referring now to the drawings, an apparatus or system according to an example embodiment is described hereinafter.

A description is now given of a light guide member according to an example embodiment, and an object detection apparatus having the light guide member with reference to the drawings.

(Object Detection Apparatus)

A description is now given of an object detection apparatus according to an example embodiment having a light guide member according to an example embodiment. In this disclosure, the object detection apparatus can be used for a vehicle-installed device control system, which is an example of device control system for a movable apparatus that controls devices installed in a vehicle such as an automobile. The vehicle may not be limited to any specific vehicles but may include various types of vehicles such as automobiles, ship, robots or the like.

Further, the object detection apparatus can be applied other than vehicle-installed device control system. For example, the object detection apparatus can be applied other systems that detect a target object adhered on a light translucent member based on captured image.

FIG. 1 is a schematic configuration of a vehicle installed with an object detection apparatus according to an example embodiment. As illustrated in FIG. 1, a vehicle 100 such as automobiles includes, for example, an object detection apparatus 101, an image analyzer 102, a headlight controller 103, a headlight 104, a windshield 105, a wiper controller 106, and a wiper 107. Further, the vehicle 100 includes, for example, a vehicle controller 108, a defroster controller 109, a defroster 110, and a temperature sensor 111.

As to the vehicle 100, based on image data of vehicle-front-area of the vehicle 100 (referred to image capturing area or a captured image area) captured by the object detection apparatus 101, lighting direction control of the headlight 104, drive control of the wiper 107, operation control of the defroster 110, and control of other devices installed in a vehicle.

The object detection apparatus 101 can capture views of vehicle-front-area of the vehicle 100 as an image capturing area or a captured image area. For example, the object detection apparatus 101 captures a vehicle-front-area of the vehicle 100 when the vehicle 100 is running. The object detection apparatus 101 is, for example, disposed near a rear-view mirror and the windshield 105 of the vehicle 100.

Image data captured by the object detection apparatus 101 is input to an image analyzer 102, which can be used as a detection processing unit.

The image analyzer 102 analyzes the captured image data, transmitted from the object detection apparatus 101, in which the image analyzer 102 can be used to compute information of other vehicle existing in a front direction of the vehicle 100 such as vehicle position, a point of the compass (e.g., north, south, east, and west), and distance to other vehicles. Further, the image analyzer 102 can be used to detect an object or substance adhered on the windshield 105 such as raindrops, foreign particles, or the like. Further, the image analyzer 102 can be used to detect a detection-target object existing on road surfaces such as a lane (e.g., white line) or the like from the image capturing area.

The image analyzer 102 has a function to control an image capture operation of the object detection apparatus 101, and a function to analyze captured image data transmitted from the object detection apparatus 101.

The image analyzer 102 has a function to set suitable exposing light quantity (e.g., exposing time) or each of target objects captured by the image sensor. The image analyzer 102 analyzes the captured image data, transmitted from the object detection apparatus 101, in which the image analyzer 102 can be used to compute suitable exposing light quantity for each of target objects captured by an image sensor such as other vehicle existing in a front direction of the vehicle 100, raindrop, frozen portion and fogging adhered on the windshield 105.

Further, the image analyzer 102 has a function to adjust light emission timing of a light source unit by linking with adjustment of exposing light quantity.

The analysis result of the image analyzer 102 can be transmitted to the headlight controller 103, the wiper controller 106, the vehicle controller 108 and the defroster controller 109.

The headlight controller 103 controls the headlight 104 to prevent a projection of high intensity light of headlight of the vehicle 100 to eyes of drivers of front-running vehicles and oncoming vehicles, by which the drivers of other vehicles are not dazzled by light coming from the headlight of the vehicle 100 while providing the enough field of view for the driver of vehicle 100.

Specifically, for example, a switching control of high beam/low beam of the headlight 104 is conducted, and a light-dimming control is partially conducted for the headlight 104 to prevent a projection of high intensity light of headlight of the vehicle 100 to eyes of drivers of front-running vehicles and oncoming vehicles, by which the drivers of other vehicles are not dazzled by light coming from the headlight of the vehicle 100 while providing the enough field of view for the driver of vehicle 100.

The wiper controller 106 controls the wiper 107 to remove an adhered object or substance adhered on the windshield 105 such as raindrops, foreign particles, or the like from the windshield 105 of the vehicle 100. The wiper controller 106 generates control signals to control the wiper 107 upon receiving the detection result of foreign particles from the image analyzer 102.

When the control signals generated by the wiper controller 106 are transmitted to the wiper 107, the wiper 107 is activated to provide the field of view for the driver of the vehicle 100.

The vehicle controller 108 controls the driving of the vehicle 100 based on a detection result of road end and white line detected by the image analyzer 102. If the vehicle 100 deviates or departs from the vehicle lane, defined by the lane (e.g., white line) and road end, based on the detection result of the lane detected by the image analyzer 102, the vehicle controller 108 activates an alarm or warning to the driver of the vehicle 100, and activates a cruise control system such as controlling of a steering wheel and/or brake of the vehicle 100.

Further, based on a detection result of road traffic signs detected by the image analyzer 102, the vehicle controller 108 can compare information of road traffic signs and vehicle running conditions. For example, if the vehicle controller 108 determines that a driving speed or vehicle running conditions of the vehicle 100 is close to a speed limit (information of road traffic signs), the vehicle controller 108 activates a cruise control system such as alarming or warning to the driver of the vehicle 100, and if the vehicle controller 108 determines that a driving speed of the vehicle 100 exceeds a speed limit, the vehicle controller 108 activates a cruise control system such as controlling of a brake of the vehicle 100.

The defroster controller 109 controls the defroster 110. Specifically, based on a detection result of the windshield 105 such as frozen and fogging conditions, the defroster controller 109 generates control signals for controlling the defroster 110. Upon receiving the control signals generated by the defroster controller 109, the defroster 110 sends air to the windshield 105 and heats the windshield 105 based on the control signals to the windshield 105 so that frozen or fogging conditions are removed.

Further, the vehicle 100 is provided with a temperature sensor 11 to detect ambient temperature. The image analyzer 102 uses a detection result of the temperature sensor 111 as required to conduct the above described various processing. In an example embodiment, a detection result of the temperature sensor 111 can be used to detect whether the windshield 105 is frozen, which will be described later.

Figure 2:
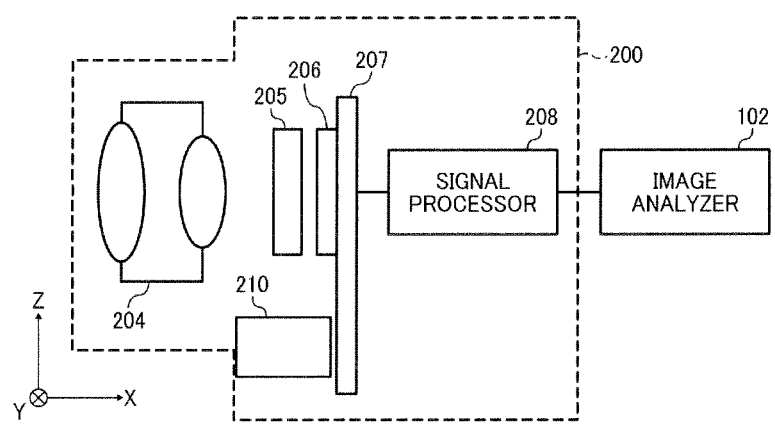
FIG. 2 is a schematic configuration of the object detection apparatus of FIG. 1.
Figure 3:
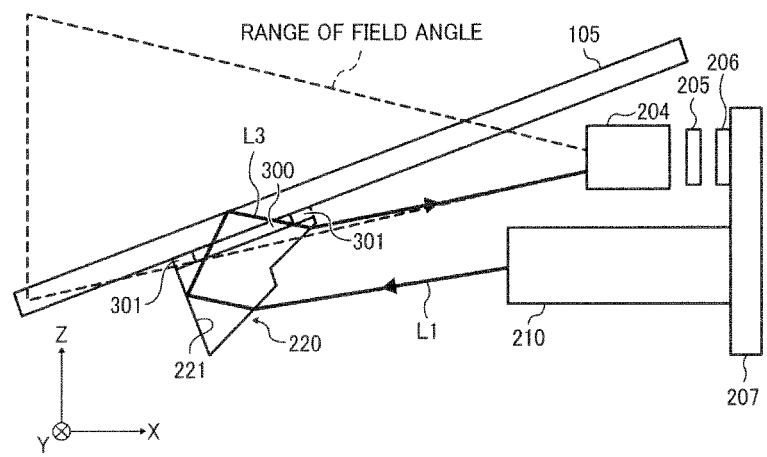
FIG. 3 is a cross-sectional view of the object detection apparatus.

FIG. 2 is a schematic configuration of the object detection apparatus 101, and FIG. 3 is a cross-sectional view of the object detection apparatus 101. As illustrated in FIG. 2 and FIG. 3, the object detection apparatus 101 includes, for example, a capture lens 204, an optical filter 205, an image sensor 206, a sensor board 207, a signal processor 208, a light source unit 210, a reflective deflection prism 220, and a first intervening member 300 and a second intervening member 301.

In an example embodiment shown in FIG. 2, the optical axis of the capture lens 204 is disposed in the object detection apparatus 101 by aligning the optical axis of the capture lens 204 to the horizontal direction, but not limited hereto, but the optical axis of the capture lens 204 can be set to a given direction with respect to the horizontal direction (X direction in FIG. 2) used as the reference direction.

The capture lens 204 can be configured with, for example, a plurality of lenses, and has a focal position set at a position far from the windshield 105. The focal position of the capture lens 204 can be set, for example, at infinity or between infinity and the windshield 105.

The optical filter 205 is disposed after the capture lens 204 to limit or regulate a wavelength range of light entering the image sensor 206.

The optical filter 205 is used to suppress an effect of ambient light coming from the outside of the vehicle when detecting the condition of the windshield 105 using a reflection light, generated by reflection of light emitted from the light source unit 210. If the conditions of the windshield 105 can be detected with good enough detection precision, the optical filter 205 can be omitted.

The image sensor 206 is an image capturing device having a pixel array arranged two-dimensionally, and the image sensor 206 can be used as a detection unit of the object detection apparatus. The image sensor 206 is composed of a plurality of light receiving elements arranged two-dimensionally to receive light passing through the optical filter 205, and each light receiving elements (or image capturing pixel) has a function of photoelectric conversion of incident light.

For example, the image sensor 206 is composed of about several hundreds of thousands of pixels arranged two-dimensionally. The image sensor 206 is a sensor employing, for example, a charge coupled device (CCD), a complementary metal oxide semiconductor (CMOS), or the like.

Light coming from the image capturing area, including an object (or detection-target object), passes the capture lens 204 and the optical filter 205, and then the image sensor 206 photo electrically converts the received light to electrical signals based on the light quantity. When the signal processor 208 receives electrical signals such as analog signals (i.e., quantity of incident light to each of light receiving elements of the image sensor 206) output from the sensor board 207, the signal processor 208 converts the analog signals to digital signals to be used as captured image data.

The signal processor 208 is electrically connected with the image analyzer 102. Upon receiving the electrical signals (analog signals) from the image sensor 206 via the sensor board 207, the signal processor 208 generates digital signals (captured image data), based on the received electrical signals, indicating luminance data for each image capturing pixel of the image sensor 206.

The signal processor 208 outputs the captured image data to a later stage unit such as the image analyzer 102 with horizontal/vertical synchronization signals of image.

The light source unit 210 is disposed on the sensor board 207. The light source unit 210 irradiates light to detect foreign particles adhered on a surface of the windshield 105 (e.g., raindrops, frozen, fogging). In this description, raindrop is used as an example of adhered foreign particles to be detected.

The light source unit 210 includes a plurality of light emitting elements such as light emitting diodes (LED) but not limited hereto. By disposing a plurality of light emitting elements, a detection area of foreign particles on the windshield 105 can be enlarged, and detection precision of condition change of the windshield 105 can be enhanced compared to using one light emitting element.

The light source unit 210 is composed of, for example, one or more light emitting diodes (LED) or laser diodes (LD).

In an example embodiment, the light source unit 210 and the image sensor 206 are installed on the same sensor board 207, with which the number of boards can be reduced compared to installing the light source unit 210 and the image sensor 206 on different boards, with which less expensive cost can be achieved.

Further, as to the light source unit 210, a plurality of light emitting points can be arranged one row or a plurality of rows along the Y direction in FIG. 2. With this arrangement, the light used for capturing an image on the windshield 105, which is below an image area for displaying an image captured for a front direction of the vehicle 100, can be set as uniform light.

The light source unit 210 is disposed on the sensor board 207 to set a given angle between the optical axis direction of the light emitted from the light source unit 210 and the optical axis direction of the capture lens 204. Further, the light source unit 210 is disposed at a position to set an irradiation area on the windshield 105 illuminated by the light emitted from the light source unit 210 is corresponded to a range of field angle (or a range of viewing angle) of the capture lens 204.

The light source unit 210 is composed of, for example, one or more light emitting diodes (LED) or laser diodes (LD). The emission wavelength of the light source unit 210 is preferably light other than the visible light so that drivers of oncoming vehicles and foot passengers are not dazzled. For example, light that has a wavelength window longer than a wavelength window of the visible light and can be sensed by the image sensor 206 is used. For example, infrared light having the wavelength window of 800 nm to 1000 nm can be used. The drive control of the light source unit 210 such as emission timing control may be conducted using the image analyzer 102 while linked with obtaining of image signals from the signal processor 208.

Conditions of reflection light reflected on the windshield 105 change depending on the condition change of the windshield 105 (e.g., raindrops adhered on the outer face of the windshield 105, frozen portion that evening dew is frozen, fogging on the inner face of the windshield 105 due to moisture).

The condition change of reflection light can be determined by analyzing the captured image captured by the image sensor 206 via the optical filter 205.

As to the object detection apparatus 101, by aligning the optical axis of the LED 211 of the light source unit 210 and a normal direction of the image sensor 206 to the normal direction of the same sensor board 207, the manufacturing process can be simplified.

However, because the light irradiation direction of the light source unit 210 and the image capturing direction of the image sensor 206 (i.e., optical axis direction of the capture lens 204) are different directions, it is difficult to dispose the light source unit 210 and the image sensor 206 on the same sensor board 207 while setting different directions for the light irradiation direction of the light source unit 210 and the image capturing direction of the image sensor 206.

Therefore, when the LED of the light source unit 210 and the image sensor 206 of the object detection apparatus 101 are disposed on the same sensor board 207, for example, a light path changing member such as a tapered light guide 215, to be describe later, can be disposed on the light source unit 210 to change a light path of light emitted from the LED 211.

Figure 4:
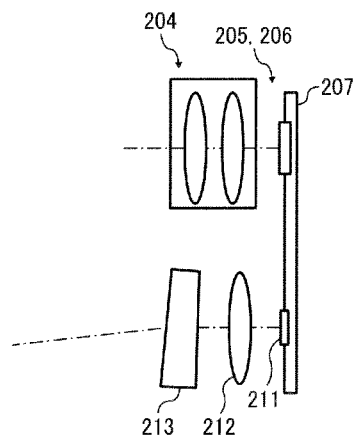
FIG. 4 is a cross-sectional view of configuration of another image capturing unit of the object detection apparatus.
Figure 5:
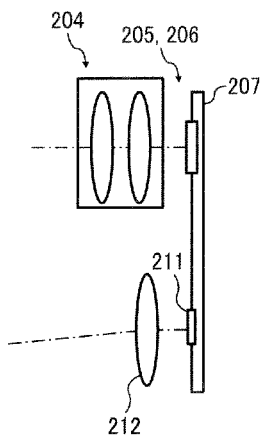
FIG. 5 is a cross-sectional view of configuration of further another image capturing unit of the object detection apparatus.

FIG. 4 is a cross-sectional view of configuration of another image capturing unit, and FIG. 5 is a cross-sectional view of configuration of further another image capturing unit. The light path changing member is, for example, a deflection prism 213 as illustrated in FIG. 4, and a collimator lens 212 disposed eccentrically as illustrated in FIG. 5.

When the collimator lens 212 is used, the number of the collimator lens 212 is required to be the same of the number of the LED 211, in which a lens array arranging the collimator lenses 212 in a straight line along the Y direction can be used.

Figure 6:
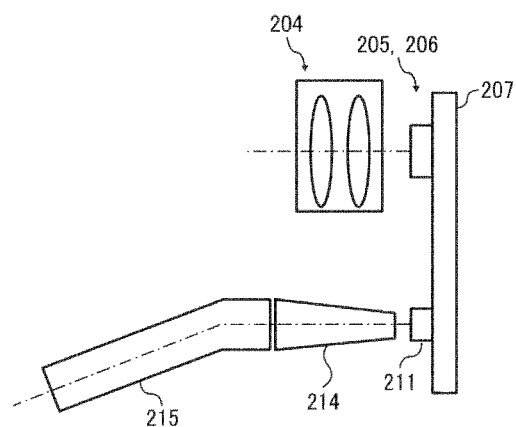
FIG. 6 is a schematic view of another light guide member of the object detection apparatus.

FIG. 6 is a schematic view of another light guide member of the object detection apparatus 101, which can be used as the light path changing member. In FIG. 6, a tapered rod lens 214 is disposed at the exit side of a plurality of LEDs 211 installed on the sensor board 207.

With this configuration, the light emitted from the LED 211 reflects on the inner face of the tapered rod lens 214 while passing through the tapered rod lens 214, and the light exits from the tapered rod lens 214 while setting the light substantially parallel to the optical axis direction of the LED 211.

Therefore, by disposing the tapered rod lens 214, a radiation angle range of light can be set small for the object detection apparatus 101.

Further, the exit side of the tapered rod lens 214 is disposed with a tapered light guide 215 that can direct the light emitted from the light source unit 210 to a desired direction. As for the configuration of FIG. 6, the light having a narrower illumination range and uniform light can be irradiated to a desired direction.

Therefore, as to the object detection apparatus 101, image or conditions of the windshield 105 can be detected with high precision, and the processing load such as correction of uneven brightness can be reduced.

As described above, as to the object detection apparatus 101, the light source unit 210 and the image sensor 206 are installed on the same sensor board 207, but the light source unit 210 and the image sensor 206 can be installed on different boards.

As illustrated in FIG. 3, the object detection apparatus 101 includes an optical member such as a reflective deflection prism 220 having a reflection face 221, wherein the reflective deflection prism 220 can be used as the light guide member for the present invention. The light emitted from the light source unit 210 can be reflected at the reflection face 221 and then guided to the windshield 105.

The reflective deflection prism 220 has one face attached firmly to the inner face of the windshield 105 using the intervening member 300 so that the light emitted from the light source unit 210 can be guided to the windshield 105 effectively.

The reflective deflection prism 220 is attached to the inner face (first face) of the windshield 105 with a condition to maintain that a regular reflection light reflected regularly at a non-adhering area, where the detection target object such as raindrop does not adhere, on the outer face (second face) of the windshield 105 can be received by the image sensor 206 even when the incident angle of the light of the light source unit 210 entering the reflective deflection prism 220 changes within a given range.

Further, the refractive index of the intervening member 300 is preferably between the refractive index of the reflective deflection prism 220 and the refractive index of the windshield 105 to reduce Fresnel reflection loss between the intervening member 300 and the reflective deflection prism 220, and between the intervening member 300 and the windshield 105 for the object detection apparatus 101. The Fresnel reflection is a reflection that occurs between materials having different refractive indexes.

Further, as illustrated in FIG. 3, the reflective deflection prism 220 regularly reflects an incident light from the light source unit 210 for one time at the reflection face 221 to direct the reflection light to the inner face of the windshield 105. The reflection light can be configured to have an incidence angle $\theta$ (e.g., $\theta \geq$ about 42 degrees) with respect to the outer face of the windshield 105.

This incidence angle $\theta$ is a critical angle that causes a total reflection on the outer face (second face) of the windshield 105 based on a difference of refractive indexes between air and the outer face of the windshield 105.

Therefore, when foreign particles such as raindrops do not adhere on the outer face (second face) of the windshield 105, the reflection light reflected at the reflection face 221 of the reflective deflection prism 220 does not pass through the outer face (second face) of the windshield 105 but totally reflected at the outer face (second face) of the windshield 105.

In contrast, when foreign particles such as raindrops having refractive index of 1.38, different from air having refractive index of 1, adhere on the outer face of the windshield 105, the total reflection condition does not occur, and the light passes through the outer face of the windshield 105 at a portion where raindrops adhere.

Therefore, the reflection light reflected at a non-adhering portion of the outer face of the windshield 105 where raindrop does not adhere can be received by the image sensor 206 as an image having high intensity or luminance. In contrast, the quantity of the reflection light decreases at an adhering portion of the outer face of the windshield 105 where raindrop adheres, and thereby the light quantity received by the image sensor 206 decreases, and the reflection light received by the image sensor 206 becomes an image having low intensity or luminance. Therefore, a contrast between the raindrop-adhering portion and the raindrop-non-adhering portion on the captured image can be obtained, with which raindrop can be detected.

Figure 7:
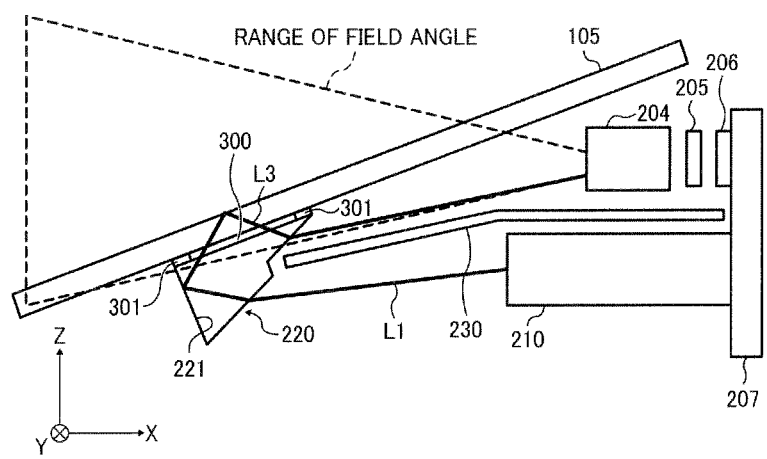
FIG. 7 is a cross-sectional view of another object detection apparatus.

FIG. 7 is a cross-sectional view of another object detection apparatus. As illustrated in FIG. 7, a light block member 230 can be disposed between the light source unit 210 and the capture lens 204 to prevent intrusion of diffused light component of the light source unit 210 to the image sensor 206. If the diffused light enters the image sensor 206, image signals may deteriorate.

Figure 8:
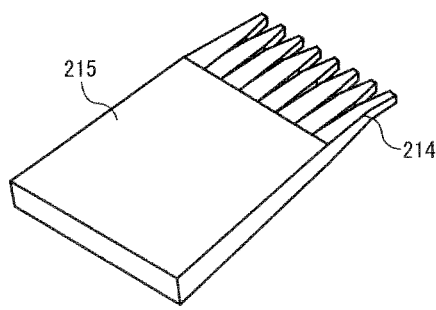
FIG. 8 is a perspective view of a light guide member of the object detection apparatus.

FIG. 8 is a perspective view of the tapered light guide 215 used as the light path changing member 215 of the object detection apparatus 10. As illustrated in FIG. 8, the light path changing member 215 can include the taper rod lens 214 at the side of the light source unit 210.

The taper rod lens 214 is disposed for LEDs as one-to-one relationship with LEDs (i.e., one taper rod lens for one LED). The taper rod lens 214 may include a mirror tube having an inner face as a reflection face.

The taper rod lens 214 is tapered from an incident face side to an exit face side such as the exit face side is greater than the incident face side. The taper rod lens 214 is preferably made of materials having a refractive index of one or more, for example, resin or glass. The taper rod lens 214 can be manufactured with less expensive cost by integrally forming resin using the molding process.

(Configuration of Reflective Deflection Prism)

Figure 9:
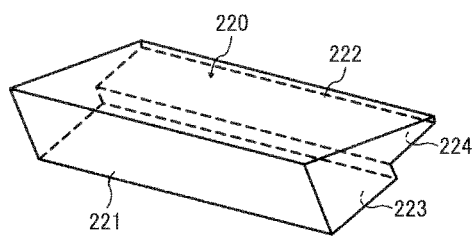
FIG. 9 is a perspective view of a reflective deflection prism of the object detection apparatus.

FIG. 9 is a perspective view of the reflective deflection prism 220 of the object detection apparatus 101. As illustrated in FIG. 9, the reflective deflection prism 220 includes, for example, an incidence face 223, a reflection face 221, a contact face 222, an exit face 224, and a light guiding portion. The exiting light and reflection light proceed in the light guiding portion. The reflective deflection prism 220 can be used as the light guide member for the present invention.

In a configuration of FIG. 9, the incidence face 223 and the exit face 224 are configured as parallel faces with each other, but the incidence face 223 and the exit face 224 are configured as non-parallel faces.

The light L1 emitting from the light source unit 210 enters the incidence face 223 via the taper rod lens 214 and the light path changing member 215.

The light L1 entering from the incidence face 223 is reflected on the reflection face 221.

The contact face 222 is attached firmly to the inner face of the windshield 105, and the contact face 222 can be used as the detection face of the light guide member for the present invention.

The light L1 emitted from the light source unit 210 and reflected by the windshield 105 passes an area of the contact face 222 as reflection light L3, which is to enter the image sensor 206. The area of the contact face 222 where the reflection light L3 passes is referred to as a detection area.

The reflection light L3 reflected at the outer face of the windshield 105 exits from the exit face 224 toward the object detection apparatus 101.

The reflective deflection prism 220 can be made of materials that can pass through the light coming from the light source unit 210 such as glass, plastic, or the like.

If the light coming from the light source unit 210 is infrared light, the reflective deflection prism 220 can be made of materials of dark color that can absorb visible lights. By employing materials that can absorb the visible light, it can reduce the intrusion of light (e.g., visible light from outside), which is other than the light coming from a LED (e.g., infrared light), to the reflective deflection prism 220.

(Configuration of Contact Face of Reflective Deflection Prism)

A description is given of the contact face 222 of the reflective deflection prism 220.

Figure 10:
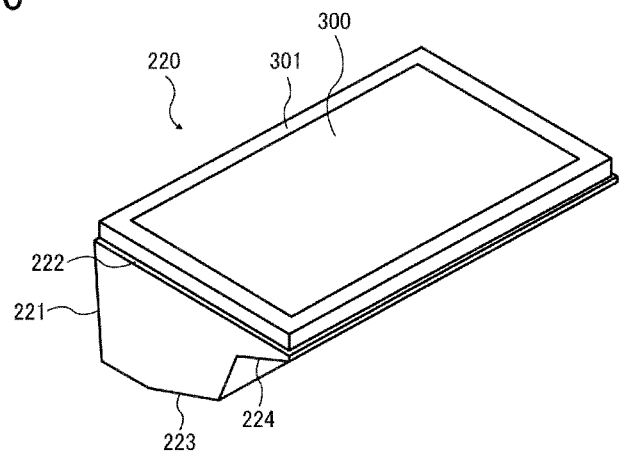
FIG. 10 is a perspective view of a contact face of the reflective deflection prism.

FIG. 10 is a perspective view of the contact face 222 of the reflective deflection prism 220. As illustrated in FIG. 10, the contact face 222 pasted with a first intervening member 300 and a second intervening member 301 in advance.

Figure 11:
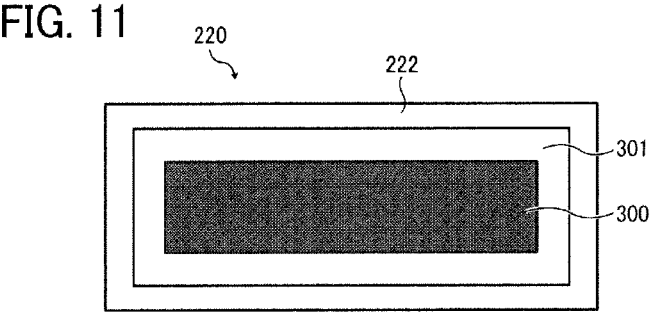
FIG. 11 is a plan view of the contact face of the reflective deflection prism.

FIG. 11 is a plan view of the contact face 222 of the reflective deflection prism 220. As illustrated in FIG. 11, the first intervening member 300 is pasted at a given area of the center portion of the contact face 222. Further, the second intervening member 301 is pasted at a periphery of the contact face 222, which is also a periphery of the first intervening member 300.

As to the contact face 222, the first intervening member 300 has an area corresponding to a detection area of adhered object used by the object detection apparatus 101. A part or entire of the detection area can be attached to a rear face of the windshield 105 via the first intervening member 300.

Light L1 emitted from the light source unit 210 and reflected by the windshield 105 passes through the contact face 222 and enters the image sensor 206 as light L3. The detection area is an area on the contact face 222 where the light L3 passes through.

The first intervening member 300 is made of, for example, material having higher flexibility such as adhesive sheet of silicone resin that can pass through light L1 such as infrared light emitted from the light source unit 210 and has higher modulus of elasticity and greater thickness.

As to the contact face 222, the second intervening member 301 pasted at an area outside the detection area of adhered object used for the object detection apparatus 101, which may be referred to as a non-detection area. A part or entire of the non-detection area can be attached to a rear face of the windshield 105 via the second intervening member 301.

The non-detection area is an area on the contact face 222 where light L3 to enter the image sensor 206 does not pass through, which means light not to enter the image sensor 206 passes through the non-detection area.

Further, the second intervening member 301 can be disposed to encircle the periphery of the first intervening member 300. By disposing the second intervening member 301 at the periphery of the first intervening member 300, the contact face 222 can be attached to an attachment face of the windshield 105 more effectively and securely.

The second intervening member 301 preferably uses material having adhesive power greater than material used for the first intervening member 300 to fix the contact face 222 on the attachment face of the windshield 105.

Further, as to the material used for the first intervening member 300 and the material used for the second intervening member 301, flexibility of the material of the first intervening member 300 is set greater than flexibility of the material of the second intervening member 301.

Further, height (or thickness) of the first intervening member 300 is preferably set higher than height (or thickness) of the second intervening member 301.

In this configuration, because the flexibility of the first intervening member 300 is greater than the flexibility of the second intervening member 301, deformation level of the first intervening member 300 can be greater than deformation level of the second intervening member 301. Therefore, the first intervening member 300 can deform in line with curvature of the windshield 105.

In this configuration, the first intervening member 300 and the windshield 105 can be contacted securely and closely, with which the contact face 222 can be contacted securely and closely to the windshield 105 via the first intervening member 300.

Figure 12:
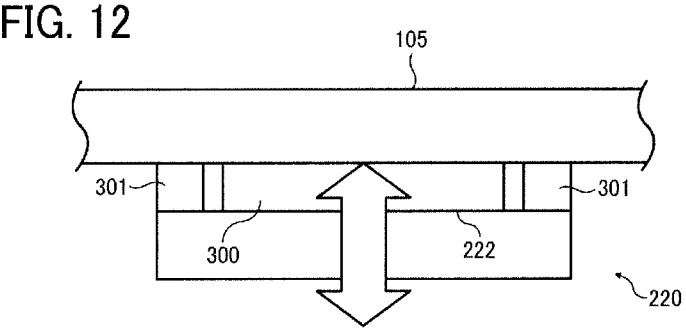
FIG. 12 is a cross-sectional view along a vehicle width direction after attaching the contact face to a windshield of a vehicle.

FIG. 12 is a cross-sectional view along a vehicle width direction after attaching the contact face 222 to the windshield 105. As illustrated in FIG. 12, as to the contact face 222, the detection area is attached to a rear face of the windshield 105 via the first intervening member 300 having higher flexibility, and the non-detection area is attached to a rear face of the windshield 105 via the second intervening member 301 having lower flexibility.

By conducting vacuum degassing to the contact face 222 pasted with the first intervening member 300 and the second intervening member 301, air bubble intruded between the contact face 222 and the first intervening member 300/ second intervening member 301 during the pasting with the contact face 222 can be removed or released.

Further, the contact face 222 and the first intervening member 300/second intervening member 301 can be pasted in vacuum to obtain the same effect of vacuum degassing.

A description is given of a shape of the contact face 222 of the reflective deflection prism 220.

Figure 13:
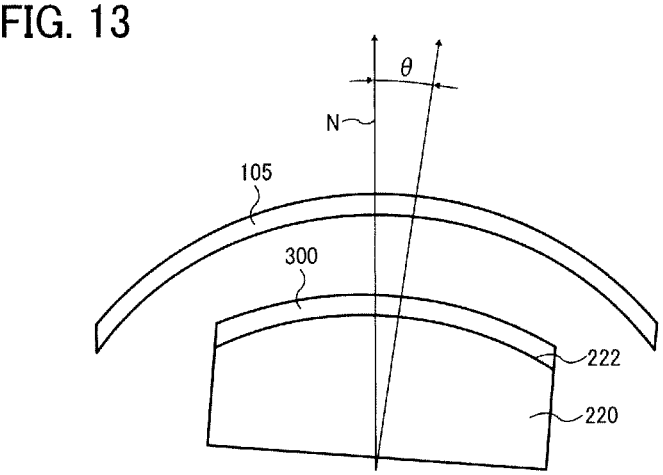
FIG. 13 is a cross-sectional view of the windshield along a vehicle width direction before attaching the reflective deflection prism to the windshield.

FIG. 13 is a cross-sectional view along a vehicle width direction before attaching the reflective deflection prism 220 to the windshield 105. FIG. 13 is a cross-sectional view of the windshield 105 along a vehicle width direction before attaching the reflective deflection prism 220 to the windshield 105.

As illustrated in FIG. 13, the windshield 105 of the vehicle 100 is designed as a curved member. Therefore, an inner face of the windshield 105 (i.e., a face facing inside the vehicle 100) is a concave face having curvature along a vehicle width direction.

The contact face 222 is a convex face having curvature corresponding to curvature of the windshield 105 in the long side direction of an area where reflection light passes through. As to the contact face 222, the detection area where reflection light passes through is set as the center of curvature.

The reflective deflection prism 220 having the contact face 222 passed with the first intervening member 300 and the second intervening member 301 in advance can be attached to the windshield 105 in the normal line direction N.

As to the reflective deflection prism 220, curvature A of the contact face 222B (convex face) can be set equal to curvature B of a prism-attachment face of the windshield 105 (concave face) or less, which means |curvature A|≤|curvature B|.

In this case, as to the reflective deflection prism 220, the windshield 105 and the first intervening member 300 can be effectively and securely attached near the center of the contact face 222B without an effect of the attachment angle θ (see FIG. 13) to the windshield 105.

The detection area of adhered object used for the object detection apparatus 101 is typically an area near the center of the contact face 222 of the reflective deflection prism 220. In this configuration, even if the space occurs to a portion other than the center of the contact face 222 (e.g., both ends of vehicle width direction) after attaching the reflective deflection prism 220 to the windshield 105, detection sensitivity of the object detection apparatus 101 is not affected by the space.

As to the reflective deflection prism 220, by setting the curvature A of the contact face 222 smaller than the curvature B of the windshield 105, the reflective deflection prism 220 can be effectively and securely contacted to the windshield 105 near the center of the contact face 222 (convex face).

Further, as to the reflective deflection prism 220, an intrusion of air bubble to the center of the contact face 222, used as the detection area of adhered object, can be suppressed, and even if air bubble intrudes, air bubble can be removed or released by applying pressure.

Therefore, as to the reflective deflection prism 220, deterioration of detection sensitivity set by attaching the reflective deflection prism 220 to the windshield 105 can be prevented.

As to the contact face 222, the first intervening member 300 having higher flexibility can deform in line with the curvature of the windshield 105 having a three-dimensional curved face, with which the detection area can be contacted securely or closely to the windshield 105 via the first intervening member 300.

Further, the contact face 222 is also attached to the windshield 105 using the second intervening member 301 having lower flexibility compared to the flexibility of the first intervening member 300. Therefore, when inertia force effects, deviation of relative position of the reflective deflection prism 220 and other optical elements such as the image sensor 206 can be suppressed.

Therefore, as to the reflective deflection prism 220 having the contact face 222 pasted with the first intervening member 300 and the second intervening member 301, false detection of raindrop due to inertia force can be suppressed, and detection performance of the object detection apparatus 101 can be improved, in which detection performance of the object detection apparatus 101 can be secured at good enough level.

(Configuration of Contact Face of Reflective Deflection Prism of Comparison Example)

A description is given of a configuration of a contact face of a reflective deflection prism 220A of a comparison example.

Figure 14:
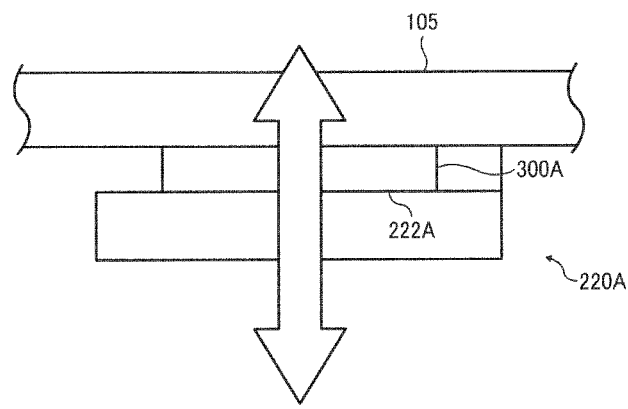
FIG. 14 is a cross-sectional view along a vehicle width direction after attaching a reflective deflection prism of comparison example to a windshield of a vehicle.
Figure 15:
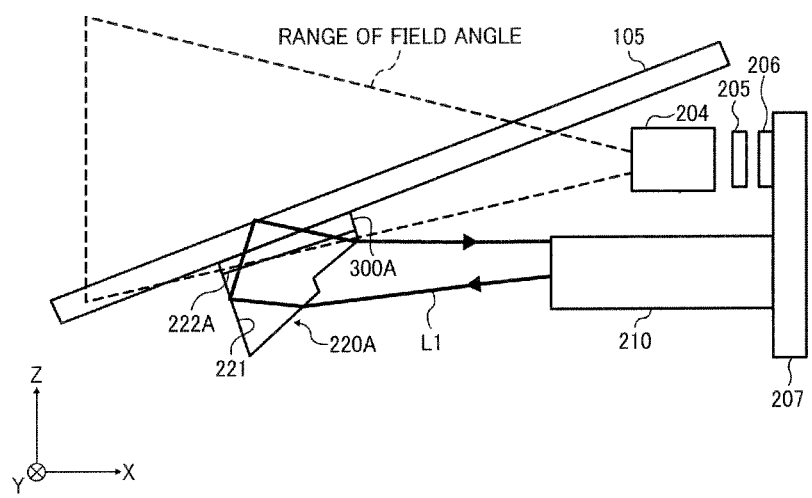
FIG. 15 is a cross-sectional view of the reflective deflection prism of FIG. 14.

FIG. 14 is a cross-sectional view along a vehicle width direction after attaching the reflective deflection prism 220A to the windshield 105 of the vehicle. FIG. 15 is a cross-sectional view of the reflective deflection prism 220A.

As illustrated in FIGS. 14 and 15, the reflective deflection prism 220A attached to the attachment face of the windshield 105 only via an intervening member 300A of the contact face 222A.

As to the reflective deflection prism 220A, the intervening member 300A having higher flexibility is used to secure close contact with the attachment face of the windshield 105 similar to the above described first intervening member 300.

Therefore, as to the reflective deflection prism 220A, when inertia force effects, contact level of the intervening member 300A may deteriorate, and the space such as air bubble may occur between the reflective deflection prism 220A and the attachment face of the windshield 105.

(Configuration of Reflective Deflection Prism (2))

Figure 16:
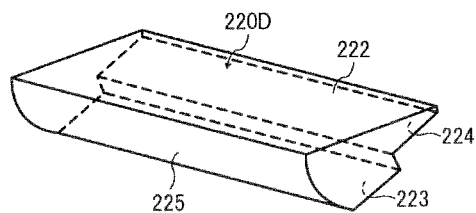
FIG. 16 is a perspective view of a reflective deflection prism according to further another example embodiment.

FIG. 16 is a perspective view of a reflective deflection prism 224D according to further another example embodiment. As illustrated in FIG. 16, the reflective deflection prism 220D has a reflection face 225 shaped in a concave face. By using the concaved reflection face 225, diffused light entering the reflection face 225 can be set parallel light in the reflective deflection prism 220D. With this configuration of the reflective deflection prism 220D, the reduction of light quantity on the windshield 105 can be suppressed.

(Configuration of Reflective Deflection Prism (3))

Figure 17:
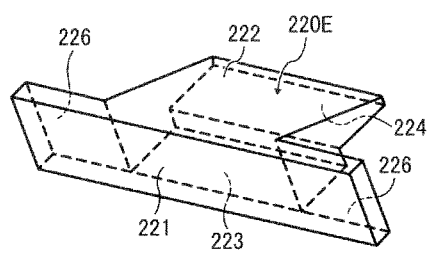
FIG. 17 is a perspective view of a reflective deflection prism according to further another example embodiment.
Figure 18:
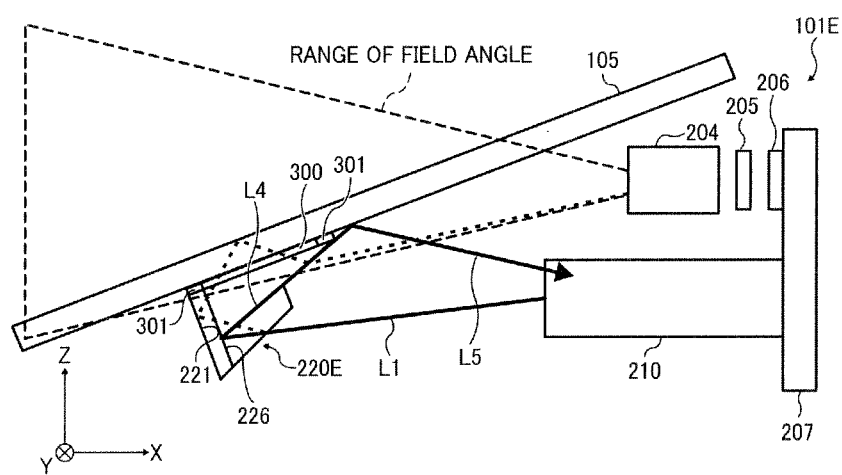
FIG. 18 is a cross-sectional view of another object detection apparatus having the reflective deflection prism of FIG. 17.

FIG. 17 is a perspective view of a reflective deflection prism 224E according to further another example embodiment. FIG. 18 is a cross-sectional view of another object detection apparatus having the reflective deflection prism 220E of FIG. 17.

The reflective deflection prism 220E can be used to detect raindrop adhered on the outer face (second face) of the windshield 105 and also to detect fogging adhered on the inner face (first face) of the windshield 105 using the light coming from the light guide member 215.

Similar to the above described the reflective deflection prism 220, as to the reflective deflection prism 220E, the light corresponding to the center portion of the reflective deflection prism 220E coming from of the light path changing member 215 enters the incidence face 223. Then, the light reflects regularly on the reflection face 221, and totally reflects on a portion where raindrop does not adhere on the outer face of the windshield 105, and is then received by the image sensor 206.

In contrast, the light corresponding to both end portion of the Y-axis direction of the reflective deflection prism 220E does not enter the incidence face 223, but totally reflects on a reflection mirror face 226 of the reflective deflection prism 220E as a total reflection light L4. The reflection light L4 is then directed to the inner face of the windshield 105. If fogging or the like does not adhere on the inner face of the windshield 105, the total reflection light L4 reflects on the inner face of the windshield 105 as a regular reflection light L5.

In this configuration, the reflective deflection prism 220E is disposed so that the regular reflection light L5 is not always received by the image sensor 206.

As to the object detection apparatus 101E, if fogging adheres on the inner face of the windshield 105, the total reflection light L4 is diffusingly reflected at the fogging portion, and the diffused reflection light is received by the image sensor 206.

Therefore, as to the object detection apparatus 101E, if an area of the image sensor 206 corresponding to the reflection mirror face 226 receives light having a given level of light quantity or more, it is determined that the diffused reflection light caused by fogging is received by the image sensor 206, with which the fogging of the inner face of the windshield 105 can be detected.

As to the reflective deflection prism 220E, the prism portion having the reflection face 221 used for detecting raindrop, and the mirror portion having the reflection mirror face 226 used for detecting fogging can be formed as one integrated unit, but can be formed as separate parts.

Further, as to the reflective deflection prism 220E, the mirror portions are disposed at both sides of the prism portion as illustrated in FIG. 17, but not limited hereto. For example, the mirror portion can be disposed at only one side of the prism portion, or at an upper or bottom of the prism portion for the light guide member of the present invention.
(Configuration of Optical Filter)

A description is given of the optical filter 205 of the object detection apparatus 101.

As to the object detection apparatus 101, when detecting raindrop on the outer face of the windshield 105, the object detection apparatus 101 captures infra-red light reflected from the windshield 105, in which the image sensor 206 receives the infra-red light emitted from the light source 210, and also ambient light coming as sun light including infra-red light having greater light quantity.

To reduce the effect of the ambient light having greater light quantity to the infra-red light coming from the light source 210, the light emission quantity of the light source 210 is required to be set greater than that of the ambient light. However, it is difficult to devise the light source 210 having the greater light emission quantity.

Figure 19:
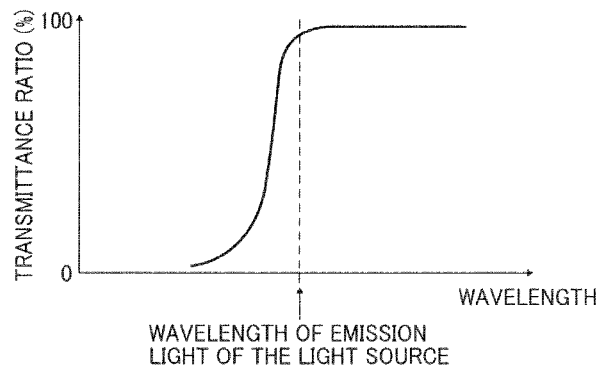
FIG. 19 is a graph of transmittance of a cut-filter and wavelength of emission light of a light source unit.

FIG. 19 is a graph of transmittance of a cut-filter and wavelength of emission light of the light source unit 210.

Figure 20:
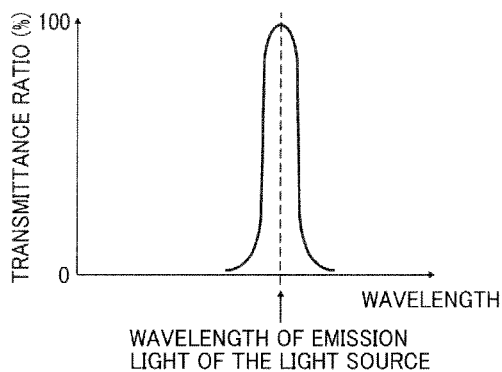
FIG. 20 is a graph of transmittance of a band-pass filter and wavelength of emission light of a light source unit.

Further, FIG. 20 is a graph of transmittance of a band-pass filter and wavelength of emission light of the light source unit 210.

In view of the above described effect of the ambient light, as to the object detection apparatus 101, a suitable cut-filter or a bend-pass filter can be used. As illustrated in FIG. 19, a cut-filter that cuts light having a wavelength smaller than a wavelength of emission light of the light source unit 210 can be used. Further, as illustrated in FIG. 20, a band-pass filter that passes through light having a specific wavelength of emission light of the light source unit 210 can be used, in which the peak of transmittance of the band-pass filter is substantially matched to the wavelength of emission light of the light source unit 210.

The image sensor 206 can effectively receive light emitted from the light source 210 using the cut-filter or band-pass filter. By using the cut-filter or band-pass filter, light having a wavelength different from the wavelength of light emitted from the light source unit 210 can be removed. Therefore, the image sensor 206 can receive the light emitted from the light source unit 210 with quantity relatively greater than quantity of the ambient light.

Therefore, without using the light source unit 210 having greater light emission intensity, the light emitted from the light source unit 210 can be effectively received by the image sensor 206 while reducing the effect of the ambient light.

As to the object detection apparatus 101, raindrop on the windshield 105 is detected based on the captured image data, and furthermore, the front-running vehicle and the oncoming vehicle are detected, and the lane (e.g., white line) is also detected based on the captured image data.

Therefore, if the light having a wavelength other than a wavelength of infra-red light emitted from the light source unit 210 is removed from an entire image, the image sensor 206 cannot receive light having a wavelength required to detect the front-running vehicle/oncoming vehicle and the lane, with which the detection of vehicle/oncoming vehicle and the lane cannot be conducted effectively.

In view of such issue, as to the object detection apparatus 101, an image area of captured image data is segmented to one detection image area used as an adhered substance detection image area, and another detection image area used as a vehicle detection image area. The adhered substance detection image area can be used to detect the raindrop 203 adhered on the windshield 105. The vehicle detection image area can be used to detect the front-running vehicle/oncoming vehicle, and the lane (e.g., white line).

Therefore, as to the object detection apparatus 101, the optical filter 205 includes a filter that can remove light having a wavelength band, which is other than infra-red light emitted from the light source 210, and the filter is disposed for the optical filter 205 only for the adhered substance detection image area.

Figure 21:
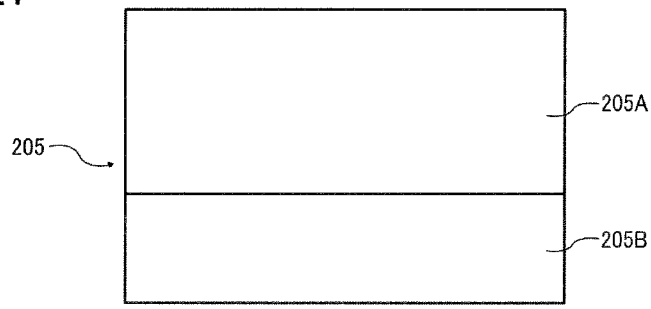
FIG. 21 is a front view of an optical filter of the object detection apparatus.
Figure 22:
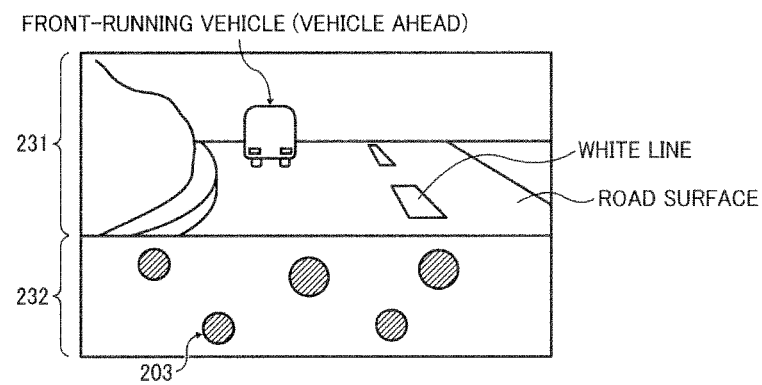
FIG. 22 is an example of image generated from captured image data using the object detection apparatus.

FIG. 21 is a front view of the optical filter 205 of the object detection apparatus 101. As illustrated in FIG. 21, the optical filter 205 includes a vehicle detection filter 205A corresponded to a vehicle detection image area 231, and an adhered substance detection filter 205B corresponded to an adhered substance detection image area 232, FIG. 22 is an example of image generated from captured image data using the object detection apparatus 101. As illustrated in FIG. 22, the vehicle detection image area 231 may be an upper two-thirds (⅔) of one image capturing area. The adhered substance detection image area 232 may be a lower one-third (⅓) of one image capturing area, in which the image capturing area can be segmented into an upper part and a lower part.

Typically, an image of headlight of the oncoming vehicle, an image of tail lamp of the front-running vehicle, an image of the lane (e.g., white line) and road traffic signs are present at the upper part of the image capturing area (i.e., vehicle-front area) while an image of road surface, which exists in the front-direction and very close to the vehicle 100, and a bonnet of the vehicle 100 are present at the lower part of the image capturing area. Therefore, information required to recognize or identify the headlight of the oncoming vehicle, the tail lamp of the front-running vehicle, and the lane is present mostly in the upper part of the image capturing area, and thereby information present in the lower part of the image capturing area may not be relevant for recognizing the oncoming vehicle, the front-running vehicle, and the lane.

Therefore, when an object detection process such as detecting the oncoming vehicle, the front-running vehicle, and/or the lane, and an adhered object detection such as raindrop 203 are to be conducted concurrently based on one captured image data, as illustrated in FIG. 22, the lower part of the image capturing area is corresponded to the adhered substance detection image area 232, and the upper part of the image capturing area is corresponded to the vehicle detection image area 231. The optical filter 205 is preferably segmented into the vehicle detection filter 205A corresponding to the vehicle detection image area 231, and the adhered object detection filter 205B corresponded to the adhered substance detection image area 232.

Further, when the image capturing direction is moved to a downward direction, a hood or bonnet of the vehicle 100 may appear at the lower part of the image capturing area. In such a case, sun light or the tail lamp of the front-running vehicle reflected on the hood of the vehicle 100 becomes ambient light. If the ambient light is included in the captured image data, the headlight of the oncoming vehicle, the tail lamp of the front-running vehicle, and the lane may not be recognized correctly.

In the object detection apparatus 101, because the cut-filter or the band-pass filter can be disposed at a position corresponding to the lower part of the image capturing area, the ambient light such as sun light, and the light of tail lamp of the front-running vehicle reflected from the hood can be removed. Therefore, the recognition precision of the headlight of the oncoming vehicle, the tail lamp of the front-running vehicle, and the lane can be enhanced.

As illustrated in FIG. 21, the optical filter 205 includes the vehicle detection filter 205A corresponded to the vehicle detection image area 231, and the adhered object detection filter 205B corresponded to the adhered object detection image area 232, and the vehicle detection filter 205A and the adhered object detection filter 205B have different layer structures.

Specifically, the vehicle detection filter 205A does not include a light separation filter layer 251, but the adhered object detection filter 205B includes the light separation filter layer 251.

Further, in the example embodiment, due to the optical property of the capture lens 204, the upside/downside of an image in the image capturing area and the upside/downside of an image in the image sensor 206 becomes opposite. Therefore, if the lower part of the image capturing area is used as the adhered object detection image area 232, the upper part of the optical filter 205 may be configured as the adhered object detection filter 205B.

The detection of the front-running vehicle can be conducted by recognizing the tail lamp of the front-running vehicle in the captured image. Compared to the headlight of the oncoming vehicle, the light quantity of the tail lamp is small. Further, ambient light such as streetlamp/streetlight or the like may exist in the image capturing area. Therefore, the tail lamp may not be detected with high precision if only the light quantity data is used.

To recognize the tail lamp effectively, spectrum information can be used. For example, based on received light quantity of the red-color light, the tail lamp can be recognized effectively. The optical filter 205 may be disposed with a red-color filter or cyan-color filter matched to a color of the tail lamp, which is a filter that can pass through only a wavelength band matched to a color used for the tail lamp, so that the received light quantity of the red-color light can be detected effectively.

However, each of the light receiving elements configuring the image sensor 206 may have sensitivity to infra-red light. Therefore, if the image sensor 206 receives light including infra-red light, the captured image may become red-color-like image as a whole. Then, it may become difficult to recognize a red-color image portion corresponding to the tail lamp.

In view of such situation, the optical filter 205 includes a light separation filter layer 255 to be described later. By employing the light separation filter layer 255, the light corresponding from the visible light to light emitted from the light source can be removed from the captured image data.

Figure 23:
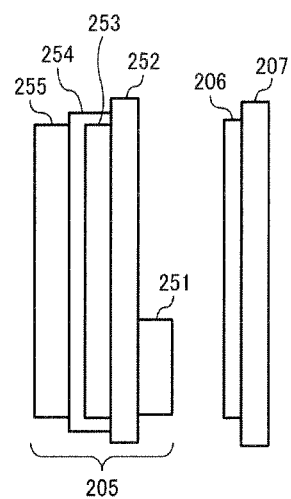
FIG. 23 is a cross-sectional view of the optical filter and an image sensor.

FIG. 23 is a cross-sectional view of the optical filter 205 and the image sensor 206. FIG. 23 is a schematic configuration of the optical filter 205 and the image sensor 206 viewed from a direction perpendicular to a light transmission direction.

The optical filter 205 is disposed close to the receiving face of the image sensor 206. As illustrated in FIG. 23, the optical filter 205 includes a transparent filter board 252. The light separation filter layer 251 is formed on one face of the transparent filter board 252 (as a face facing the receiving face of the image sensor 206), and a polarized-light filter layer 253 and the light separation filter layer 255 are formed with a given order on other face of the transparent filter board 252.

The optical filter 205 and the image sensor 206 can be bonded with each other, for example, by using ultraviolet (UV) adhesives. Further, a spacer can be disposed outside of an effective pixel area for image capturing between the optical filter 205 and the image sensor 206, and then sides of the outside of effective pixel area can be bonded by UV adhesives or heat pressing.

The filter board 252 of the optical filter 205 can be made of translucent materials, for example, glass, sapphire, quartz, matched to the use wavelength area such as the visible light range and infrared light range in an example embodiment. For example, durable less expensive glass such as quartz glass having refractive index of 1.46 and TEMPAX (registered trademark) glass having refractive index of 1.51 can be used as materials of the filter board 252.

Figure 24:
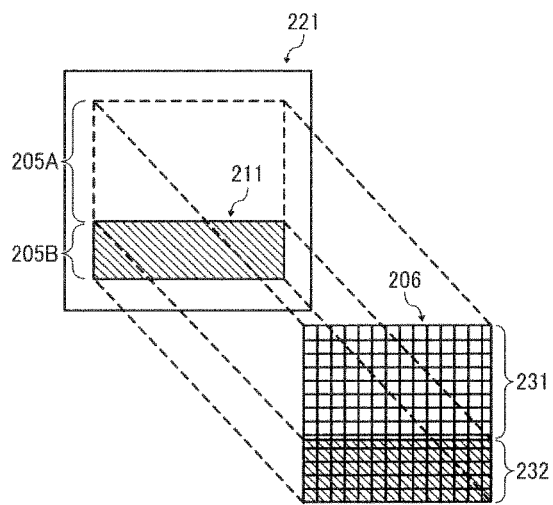
FIG. 24 is a front view of the optical filter and the image sensor.

FIG. 24 is a front view of the optical filter 205 and the image sensor 206. FIG. 24 shows a relationship of the vehicle detection filter 205A and the adhered object detection filter 205B of the optical filter 205, and the vehicle detection image area 231 and the adhered object detection image area 232 on the image sensor 206.

Figure 25:
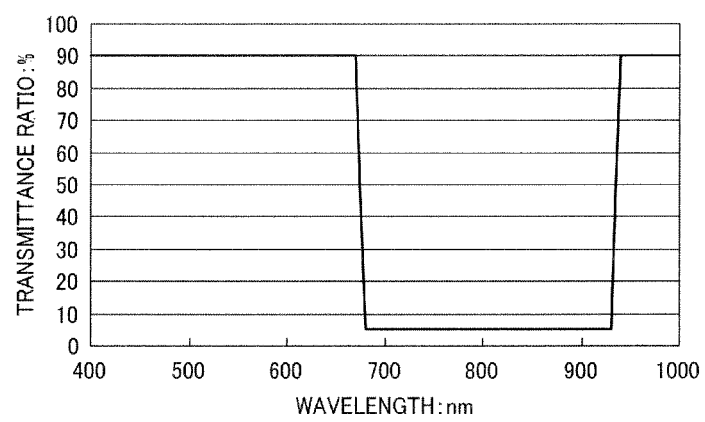
FIG. 25 is a graph of transmittance property of a light separation filter layer of the optical filter.

FIG. 25 is a graph of transmittance property of the light separation filter layer 255 of the optical filter 205. The light separation filter layer 255 of the optical filter 205 has transmittance property shown in FIG. 25.

Specifically, the light separation filter layer 255 can pass through an incident light of visible light range having a wavelength window of from 400 nm to 670 nm, and an incident light of infrared light range having a wavelength window of from 940 nm to 970 nm, and cuts an incident light having a wavelength window of from 670 nm to 940 nm.

The transmittance for the wavelength window of 400 nm to 670 nm and the wavelength window of 940 nm to 970 nm is preferably 30% or more, and more preferably 90% or more. The transmittance for the wavelength window of from 670 nm to 940 nm is preferably 20% or less, and more preferably 5% or less.

The incident light of visible light range can be used to detect a vehicle and white lane at the vehicle detection image area 231, and the incident light of infrared light range can be used to detect an adhered object such as raindrop adhered on the windshield 105 at the adhered object detection image area 232.

The incident light having a wavelength window of from 670 nm to 940 nm is cut (i.e., not passing through) because if the incident light having a wavelength window of from 670 nm to 940 is used, the image data becomes red as whole, with which it may become difficult extract the tail lamp and red-color signs having red color.

Because the light separation filter layer 255 cuts the incident light having a wavelength window of from 670 nm to 940 nm, the recognition precision of the tail lamp can be enhanced, and further, the detection precision of road traffic signs having red color such as "stop" sign used in for example Japan can be enhanced.

The wavelength window from 940 nm to 970 nm, and the wavelength window from 400 nm to 670 nm are example wavelength windows used for an example embodiment.

The light separation filter layer 255 has a multi-layered film structure formed by stacking thin films of high refractive index and thin films of low refractive index alternately. The multi-layered film structure can enhance design freedom of spectrum transmittance using interference of light, and if the thin films are stacked with a greater number, nearly 100% reflection coefficient can be achieved for a specific wavelength (e.g., wavelength other than infrared light).

The polarized-light filter layer 253 is disposed for the optical filter 205 to reduce noise caused by unnecessary reflection light. The light emitted from the light source unit 210 reflects on the inner face and outer face of the windshield 105, and the reflection light may enter the object detection apparatus 101.

This reflection light includes a polarized light component (horizontal polarized light component), which is perpendicular to a face such as the vertical face in an example embodiment defined by two optical axes such as an optical axis of the light emitted from the light source unit 210 and entering the windshield 105 and an optical axis of the capture lens 204, and this horizontal polarized light component is strong polarized light component. Therefore, the polarized-light filter layer 253 has a polarized-light filter to pass through the horizontal polarized light component and to cut a perpendicular polarized light component parallel to the vertical face.

Figure 26:
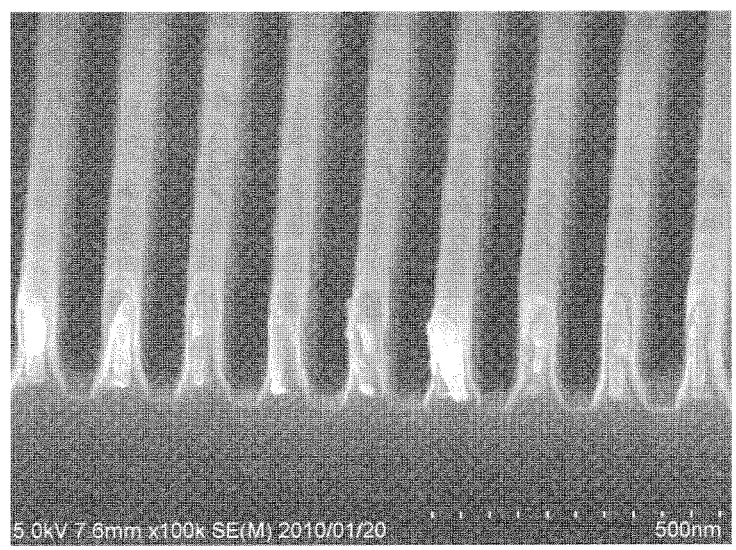
FIG. 26 a view of a polarizer having a wire grid structure.

FIG. 26 is a view of a polarizer having a wire grid structure. The polarized-light filter 253 may be a polarizer having the wire grid structure shown in FIG. 26. The wire grid structure is formed by disposing a number of conductive metal wires with a given wire pitch in a given direction. For example, the wire grid structure polarizer can be configure with a number of conductive metal wires such as aluminum wires arranged with a given wire pitch in a given direction.

By setting the wire pitch of the wire grid structure enough smaller than a wavelength of the incidence light (e.g., wavelength of visible light) such as one half ($\frac{1}{2}$) or less of wavelength of the incidence light, light having an electric field vector oscillating in parallel to the long side direction of conductive metal wire can be mostly reflected by the wire grid structure polarizer.

Further, the light having an electric field vector oscillating in perpendicular to the long side direction of conductive metal wire can be mostly passed through by the wire grid structure polarizer.

Therefore, the wire grid structure polarizer can be used as a polarizer that can generate single polarization light.

Typically, as to the polarizer having the wire grid structure, when the cross sectional area of the metal wire increases, the extinction ratio increases, and further if the metal wire has a greater width with respect to a pitch width, the transmittance decreases.

Further, as to the wire grid structure polarizer, if the cross sectional shape perpendicular to the long side direction of metal wire is a taper shape, the wavelength dispersing phenomenon for the transmittance and the polarization level become small for broader wavelength range, and thereby a high extinction ratio may be set.

The wire grid structure polarizer can be formed using known semiconductor manufacturing process. Specifically, a thin film of aluminum is deposited on a translucent filter board, and then the patterning is conducted, and the sub-wavelength convex/concave structure of the wire grid is formed by the metal etching.

By using such manufacturing process, a polarization light direction (i.e., polarization axis), can be adjusted with a size of image capture pixel of image capturing element of the image sensor 206 such as several μm level for the wire grid structure polarizer.

Further, the wire grid structure polarizer can be formed of metal material such as aluminum having good level of heat-resistance. Such wire grid structure can be preferably used under high temperature environment which may frequently occur inside vehicles or the like.

A filler agent is filled into the concave portions between the metal wires of wire grid and a space between the filter board 252 and the polarized-light filter layer 253 to form a filler layer 254. The filler agent may be preferably inorganic materials having a refractive index same or smaller than a refractive index of the filter board 252.

Material used for the filler layer 254 preferably has a low refractive index as close as the refractive index of "1" of air to prevent deterioration of polarization property of the polarized-light filter layer 253.

For example, porous ceramic materials having tiny holes dispersed in ceramics may be preferably used for the filler layer 254. Specifically, porous silica ($SiO_2$), porous magnesium fluoride (MgF), or porous alumina ($Al_2O_3$) can be used.

The refractive index can be set based on the numbers and size (i.e., porous level) of holes in ceramics. If the main component of the filter board 252 is quartz or glass of silica, porous silica (n=1.22 to 1.26) can be preferably used for the filler layer 254 because the refractive index become smaller than the filter board 252.

The filler layer 254 can be formed by applying the inorganic filler agent using the spin on glass (SOG). Specifically, a solution prepared by solving silanol (Si(OH)$_4$) into alcohol is applied on the filter board 252 using the spin coating method. Then, the solvent is evaporated by applying heat, and the silanol is reacted under the dehydrogenative polymerization reaction process to form the filler layer 254.

Because the polarized-light filter layer 253 employs the wire grid structure having a sub-wavelength size having a weak mechanical strength, which may be damaged by a small external force. The mechanical strength of the polarized-light filter layer 253 is weak compared to the light separation filter layer 255 formed on the filler layer 254.

Because the polarized-light filter layer 253 having a weak mechanical strength is covered and protected by the filler layer 254, damages to the wire grid structure of the polarized-light filter layer 253 can be reduced, suppressed, or prevented when installing the optical filter 205. Further, because the filler layer 254 is formed, an intrusion of foreign particles to the concave portions of the wire grid structure of the polarized-light filter layer 253 can be prevented.

Further, because the filler layer 254 is formed, an intrusion of foreign particles to the concave portions of the wire grid structure of the polarized-light filter layer 253 can be prevented.

Further, the height of the convex portion of wire grid structure of the polarized-light filter layer 253 is low such as one half or less of the wavelength for use.

In contrast, the height of filter layer of the light separation filter layer 255 is high such as same or several times of the wavelength for use. Further, the greater the thickness of the light separation filter layer 255, the transmittance profile can be set sharp at a cut-wavelength. The greater the thickness of the filler layer 254, the harder to secure the flatness of the top face of the filler layer 254. Further, the greater the thickness of the filler layer 254, the harder to secure the evenness of the filler layer 254. Therefore, too-thick filler layer is not preferable.

In an example embodiment, the light separation filter layer 255 is formed on the filler layer 254 after covering the polarized-light filter layer 253 by the filler layer 254, in which the filler layer 254 can be formed stably.

Further, as to the optical filter 205, the light separation filter layer 255 formed on the filler layer 254 can be formed with a preferable property.

As to the optical filter 205, the light separation filter layer 255, the filler layer 254, and the polarized-light filter layer 253 are disposed on the filter board 252 facing the capture lens 204. In general, it is important to minimize defects which may occur during the manufacturing process of these layers, and the allowable size of defect (i.e., allowable upper limit) becomes greater as farther from the image sensor 206.

The filter board 252 may have a thickness of, for example, from 0.5 mm to 1 mm.

As to the optical filter 205, by disposing the above mentioned layers are on the filter board 252 facing the capture lens 204, manufacturing process can be simplified, and manufacturing cost can be reduced compared to disposing the above mentioned layers on the filter board 252 facing the image sensor 206.

Further, as to the optical filter 205, the light separation filter layer 251 is formed on the filter board 252 facing the image sensor 206. The light separation filter layer 251 is disposed for the adhered object detection filter 205B, but not disposed for the vehicle detection filter 205A.

As described above, if the infrared light reflected at the raindrops or frozen portion on the windshield 105 is to be detected as it is, the light source unit 210 that irradiates the infrared light may need to increase the light quantity greater than the ambient light having enormous light quantity of, for example, the sunlight.

Therefore, as to the optical filter 205, the light separation filter layer 251 is formed for the adhered object detection filter 205B. The light separation filter layer 251 can be a cut filter that can cut light having a wavelength smaller than the emission wavelength of the light source unit 210, or a band-pass filter having the transmittance peak substantially matched to the emission wavelength light source unit 210.

Figure 27:
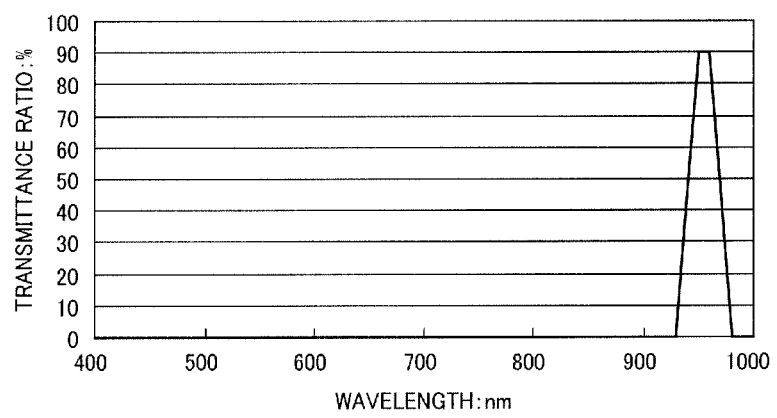
FIG. 27 is a graph of transmittance property of the light separation filter layer.

FIG. 27 is a graph of transmittance property of the light separation filter layer 251. As illustrated in FIG. 27, the light separation filter layer 251 can employ a band-pass filter having the transmittance peak substantially matched to the emission wavelength light source unit 210. With this configuration, the ambient light, which is not the emission wavelength of the light source unit 210, can be removed, and the detected light quantity originally coming from the light source unit 210 can be relatively increased.

The optical filter 205 includes two light separation filter layers such as the light separation filter layers 251 and 255, and each of the light separation filter layers 251 and 255 is formed on the each of faces of the filter board 252, which are opposite faces of the filter board 252. With this configuration, warping of the optical filter 205 can be suppressed.

If a multi-layered film structure is formed on only one face of the filter board 252, the warping of the optical filter 205 may occur due to stress to the multi-layered film structure. However, in an example embodiment, the multi-layered film structure is formed both faces of the filter board 252, with which each stress effect can be cancelled, and the warping of the optical filter 205 can be suppressed.

The light separation filter layer 251 has a multi-layered film structure formed by stacking thin films of high refractive index and thin films of low refractive index alternately, which is referred to a wavelength filter. The multi-layered film structure can enhance design freedom of spectrum transmittance using interference of light, and if the thin films are stacked with a greater number, nearly 100% reflection coefficient can be achieved for a specific wavelength.

When depositing the light separation filter layer 251 using the vapor depositing, a mask is placed to cover a portion corresponding to the vehicle detection filter 205A so that the light separation filter layer 251 is not formed on the vehicle detection filter 205A while the light separation filter layer 251 can be formed on the adhered object detection filter 205B.

Typically, color filters used for color sensors are made of resist material. However, control of spectrum properties using the resist material is difficult compared to the multi-layered film structure.

In an example embodiment, by employing the multi-layered film structure for the light separation filter layers 251 and 255, any spectrum properties can be obtained. Therefore, the passing wavelength range of the light separation filter layers 251 and 255 can be substantially matched to the wavelength range of the light of the light source unit 210.

As to the optical filter 205, the light separation filter layer 251 is disposed for suppressing the ambient light but not limited hereto. For example, raindrop can be detected using a configuration without the light separation filter layer 251.

A configuration having the light separation filter layer 251 suppressing the ambient light effect is preferable as a configuration of the optical filter 205 because the raindrop can be detected effectively by reducing the effect of ambient light, in which fluctuation caused by noise can be suppressed.

Figure 28:
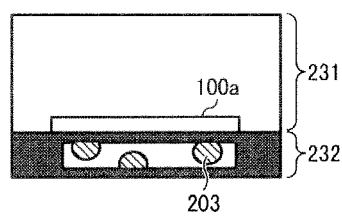
FIG. 28 is an example captured image using the reflective deflection prism of FIG. 23, in which a condition composed of adhering of raindrop and no-adhering of fogging is captured.

FIG. 28 is an example captured image using the reflective deflection prism 220E shown in FIG. 23, in which a condition composed of adhering of raindrop and no-adhering of fogging is captured.

Figure 29:
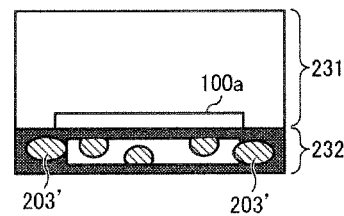
FIG. 29 is an example captured image using the reflective deflection prism of FIG. 23, in which a condition composed of adhering of raindrop and adhering of fogging is captured.

FIG. 29 is an example captured image using the reflective deflection prism 220E, in which a condition composed of raindrops adhering of raindrop and fogging adhering is captured.

When the reflective deflection prism 220E is used, some of the light L1 emitted from the light source unit 210 regularly reflects on the outer face of the windshield 105 where the raindrops 203 does not adhere as the regular reflection light L3, and then the regular reflection light L3 is received at the center portion in left/right direction of the adhered object detection image area 232, in which the portion receiving the light L3 becomes high luminance.

Further, when some of the light L1 emitted from the light source unit 210 strikes or enters the windshield 105 where the raindrops 203 adheres, the light does not reflect regularly on the outer face of the windshield 105, thereby the regular reflection light is not received at the center portion in left/right direction of the adhered object detection image area 232, in which the portion not receiving the light becomes low luminance.

In contrast, because the both end portions in left/right direction of the adhered object detection image area 232 does not receive the regular reflection light L5, the both end portions may be constantly at low luminance as illustrated in FIG. 28.

However, if fogging occurs on the inner face of the windshield 105, this fogging condition is assumed as adhering of small-sized water drops, and diffused reflection light occurs at a fogging area 203A.

By receiving this diffused reflection light, the luminance of fogging portion becomes slightly greater than the luminance of no-fogging portion as illustrated in FIG. 29

If fogging adheres on the inner face of the windshield 105, a contour or edge of a hood 100a displayed on the vehicle detection image area 231 may be blurred.

As to the object detection apparatus 101, by using this blurred edge image, it can detect whether fogging occurs.

Even if the optical filter 205 is disposed as described above, some ambient light may pass through a band-pass range of the optical filter 205 because some ambient light may have the same emission wavelength of the light source unit 210, thereby the effect of ambient light cannot be removed completely.

For example, during the day, infrared wavelength component of the sunlight affects as ambient light, and at night, infrared wavelength component included in headlight of oncoming vehicles affects as the ambient light. These ambient lights may cause a false detection when detecting the raindrop 203.

For example, an algorithm to detect the raindrops 203 is employed, in which the algorithm is used to determine that raindrop adheres at a portion where a luminance value on the adhered object detection image area 232 changes greater than a given level. However, a false detection of raindrop may occur if the luminance value is offset by the effect of ambient light.

This false detection can be prevented by controlling a light-ON timing of the light source unit 210. For example, the light-ON timing of the light source unit 210 is synchronized to an exposure timing of the image sensor 206.

Specifically, an image is captured when the light source unit 210 is set light-ON, and an image is captured when the light source unit 210 is set light-OFF for the adhered object detection image area 232 to generate a difference image of the two captured images, and then the raindrop detection is conducted based on the difference image.

Therefore, in this method, at least two frames of captured image are used to detect raindrops.

Figure 30:
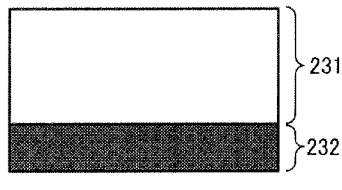
FIG. 30 is one of two frames for detecting raindrop.

FIG. 30 is one of two frames for detecting raindrop. FIG. 30 is an example of captured image for one of two frames to detect raindrop, which is captured when the light source unit is set light-OFF.

Figure 31:
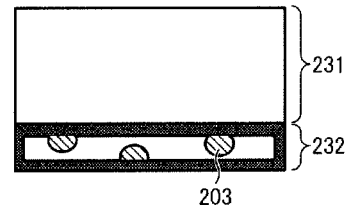
FIG. 31 is another one of two frames for detecting raindrop.

FIG. 31 is one of two frames for detecting raindrop. FIG. 31 is an example of captured image for one of two frames to detect raindrop, which is captured when the light source unit is set light-ON. When the light source unit 210 is set light-OFF, only an image of ambient light is captured for the adhered object detection image area 232.

In contrast, when the light source unit 210 is set light-ON, an image caused by ambient light and an image caused by the light source unit 210 are captured for the adhered object detection image area 232.

Therefore, luminance value (pixel value of difference image) that can be obtained by computing a difference of luminance between the two frames can remove the effect of ambient light. By conducting the raindrop detection based on this difference image, the false detection caused by ambient light can be suppressed.

Further, by setting the light-OFF for the light source unit 210 except at the light-ON timing of the light source unit 210 to detect raindrop, power consumption can be reduced preferably.

As to the ambient light, the sunlight may not change greatly along the timeline, but the light of headlight of oncoming vehicles receivable when the vehicle 100 is running may change greatly within a very short period of time.

In this case, if a time interval between the two frames to obtain the difference image is long, the value of ambient light may change during the time interval, in which when the difference image is generated, the ambient light may not be cancelled effectively. To prevent this situation, the two frames used for obtaining the difference image are preferably consecutively captured frames.

As to the object detection apparatus 101, when a normal frame to be used for image information for the vehicle detection image area 231 is captured, an automatic exposure control (AEC) is conducted based on luminance value for the vehicle detection image area 231 while the light source unit 210 is set light-OFF.

At a given timing when capturing the normal frames, the two frames used for raindrop detection are consecutively captured between the normal frames. When the two frames are captured, the exposure control suitable for raindrop detection is conducted instead of the AEC used for capturing the normal frames.

Further, when the vehicle control and light beam orientation control are conducted based on image information of the vehicle detection image area 231, the automatic exposure control (AEC) is conducted based on the luminance value at the center of captured image.

However, when capturing the two frames used for detecting raindrop, an exposure control suitable for the raindrop detection is preferably conducted. If the AEC is conducted when capturing the two frames used for the raindrop detection, an exposure time for capturing a frame when the light source unit 210 is set light-ON and an exposure time for capturing a frame when the light source unit 210 is set light-OFF may change.

If the exposure time differs between the two frames, luminance value of the ambient light included in each of the frames may change, with which the ambient light cannot be cancelled suitably using the difference image.

Therefore, the exposure control for the two frames used for detecting raindrop can be conducted, for example, by using the same exposure time for the two frames.

Further, as to the two frames for detecting raindrop, instead of using the same exposure time for the two frames, the difference image can be generated by correcting a difference of exposure time using an image processing.

Specifically, when an exposure time for a frame captured when the light source unit 210 is set light-ON is referred to as the exposure time Ta, and an exposure time for a frame captured when the light source unit 210 is set light-OFF referred to as the exposure time Tb, as shown in following formulas (1) to (3), the luminance value Ya for the light-ON frame and the luminance value Yb for the light-OFF frame are divided by respective exposure time to compute a difference value Yr.

By using the corrected difference image, even if the exposure time between the two frames may be different, the effect of ambient light can be removed effectively without an effect of the difference exposure time.

$$YA = Ya/Ta \quad (1)$$

$$YB = Yb/Tb \quad (2)$$

$$Yr = YA - YB \quad (3)$$

Further, instead of using the same exposure time for the two frames, the difference image can be generated by controlling irradiation light quantity of the light source unit 210 depending on the difference of exposure time.

In this method, the irradiation light quantity of the light source unit 210 is decreased for a frame having a long exposure time, with which without an effect of the different exposure time, the effect of ambient light can be removed effectively using the difference image of the two frames having different exposure time.

Further, as to this method of controlling irradiation light quantity or light intensity from the light source unit 210 based on the difference of exposure time, the correction by the above described image processing is not required, wherein the above described correction using the image processing may increase the processing load.

Further, the light emission output of LED 211 used as the light emitting element of the light source unit 210 changes when temperature changes. Specifically, when temperature increases, the light emission output of the light source unit 210 may decrease.

Further, the light emission quantity of the LED 211 may decrease due to aging. If the light emission output of the light source unit 210 changes or varies, such change may be recognized that luminance value changes even if raindrop does not adhere, with which a false detection of raindrop may occur.

To suppress the effect of light emission output change of the LED 211, as to the object detection apparatus 101, it is determined whether the light emission output of the LED 211 changes, and if it is determined that the light emission output of the LED 211 changes, the light emission output of the LED 211 is increased.

The change of light emission output of the LED 211 can be determined as follows. As to the object detection apparatus 101, the total reflection light L3 from the outer face of the windshield 105 is captured as a two-dimensional image at the adhered object detection image area 232. Therefore, if the change of light emission output of the LED 211 occurs, luminance of the adhered object detection image area 232 becomes lower as a whole.

Further, when the outer face of the windshield 105 is wet by rain, luminance of the adhered object detection image area 232 becomes lower as a whole. Therefore, the above two cases of lower luminance needs to be distinguished.

Therefore, when luminance of the adhered object detection image area 232 becomes lower as a whole, the wiper 107 is operated. If luminance of the adhered object detection image area 232 is still lower as a whole after operating the wiper 107, it is determined that the change of light emission output of the LED 211 occurs.

(Process of Detecting Windshield Condition)

A description is given of a process of detecting conditions of the windshield 105 with reference to FIG. 38.

Figure 32:
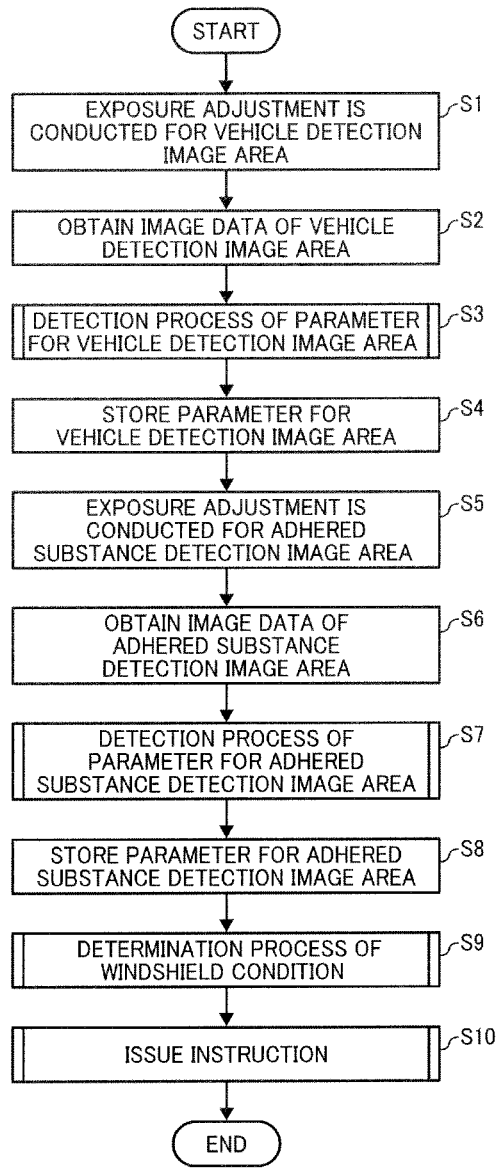
FIG. 32 is a flowchart showing the steps of a process of detecting conditions of a windshield conduct-able by the image analyzer.

FIG. 32 is a flowchart showing the steps of a process of detecting conditions of the windshield 105 conduct-able by the image analyzer 102.

Compared to the vehicle detection filter 205A not having the light separation filter layer 251, the adhered object detection filter 205B having the light separation filter layer 251 receives light with a smaller light quantity.

Therefore, the light quantity passing through the adhered object detection filter 205B and the light quantity passing through the vehicle detection filter 205A have a greater difference. Therefore, an image capturing condition (e.g., exposure value) matched to the vehicle detection image area 231 corresponding to the vehicle detection filter 205A, and an image capturing condition (e.g., exposure value) matched to the adhered object detection image area 232 corresponding to the adhered object detection filter 205B have a greater difference.

Therefore, in the image analyzer 102, different exposure values are used for capturing an image for the vehicle detection image area 231 (used for vehicle detection) and capturing an image for the adhered object detection image area 232 (used for adhered object detection).

For example, adjustment of exposure value for detecting vehicle can be conducted by conducting an automatic exposure adjustment based on an output of the image sensor 206 corresponding to the vehicle detection image area 231 (S1) while the adjustment of exposure value for adhered object detection image area 232 can be adjusted to a given set exposure value (S5).

The exposure value can be changed, for example, by changing the exposure time. The exposure time can be changed, for example, by controlling the time duration for converting the light quantity received by the image sensor 206 to electrical signals by using the image analyzer 102.

The vehicle detection image area 231 is used for capturing an image around the vehicle 100. Because the lighting condition around the vehicle changes greatly such as from several tens of thousands lux (lx) during the day to one lux or less at night, the received light quantity changes greatly depending on image capturing scenes.

Therefore, as to the vehicle detection image area 231, the exposure time is required to be adjusted based on the image capturing scenes. For example, it may be preferable to adjust the exposure value for the vehicle detection image area 231 using the known automatic exposure control (AEC).

In contrast, an image for the adhered object detection image area 232 is captured by receiving the light emitted having a given constant light quantity from the light source unit 210 through the optical filter 205 having a given transmittance, in which the received light quantity changes a little.

Therefore, the automatic adjustment of exposure value is not conducted for the adhered object detection image area 232, and an image for the adhered object detection image area 232 can be captured using a set exposure time. By using the set exposure tune, the control time of exposure value can be shortened, and the exposure value control can be simplified.

In the object detection apparatus 101, upon conducting the exposure adjustment for the vehicle detection image area 231 (S1), the image analyzer 102 obtains image data of the vehicle detection image area 231 (S2).

In the object detection apparatus 101, image data of the vehicle detection image area 231 can be used to detect vehicles, lanes (e.g., white line), road traffic signs, and also used for the wiper control and the defroster control to be described later.

Therefore, upon obtaining the image data of the vehicle detection image area 231, the image analyzer 102 detects parameter for the wiper control and the defroster control (S3), and stores the parameter to a given storage area (S4).

Figure 33:
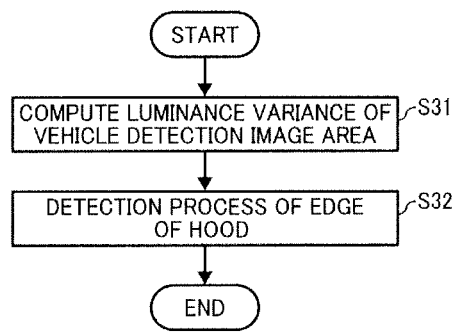
FIG. 33 is a flowchart showing the steps of a process of detecting parameter for wiper control and defroster control from image data of vehicle detection image area.

FIG. 33 is a flowchart showing the steps of a process of detecting parameter for the wiper control and the defroster control from the image data of the vehicle detection image area 231.

In the object detection apparatus 101, the value of luminance variance for the vehicle detection image area 231 is used for detecting the parameter for the wiper control and the defroster control (S31).

Further, in the object detection apparatus 101, an image capturing area is set so that an edge portion between a hood of the vehicle 100 and a background can be detected, and a result of an edge extraction of the hood is also used as a parameter (S32).

Figure 34:
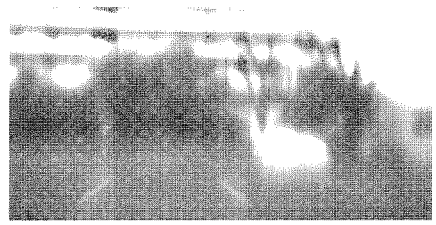
FIG. 34 is a view of fogged windshield.
Figure 35:
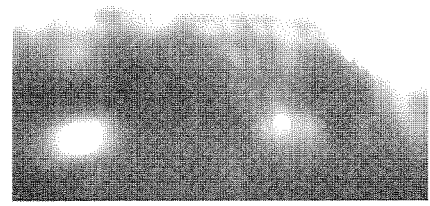
FIG. 35 is a view of frozen windshield.
Figure 41:
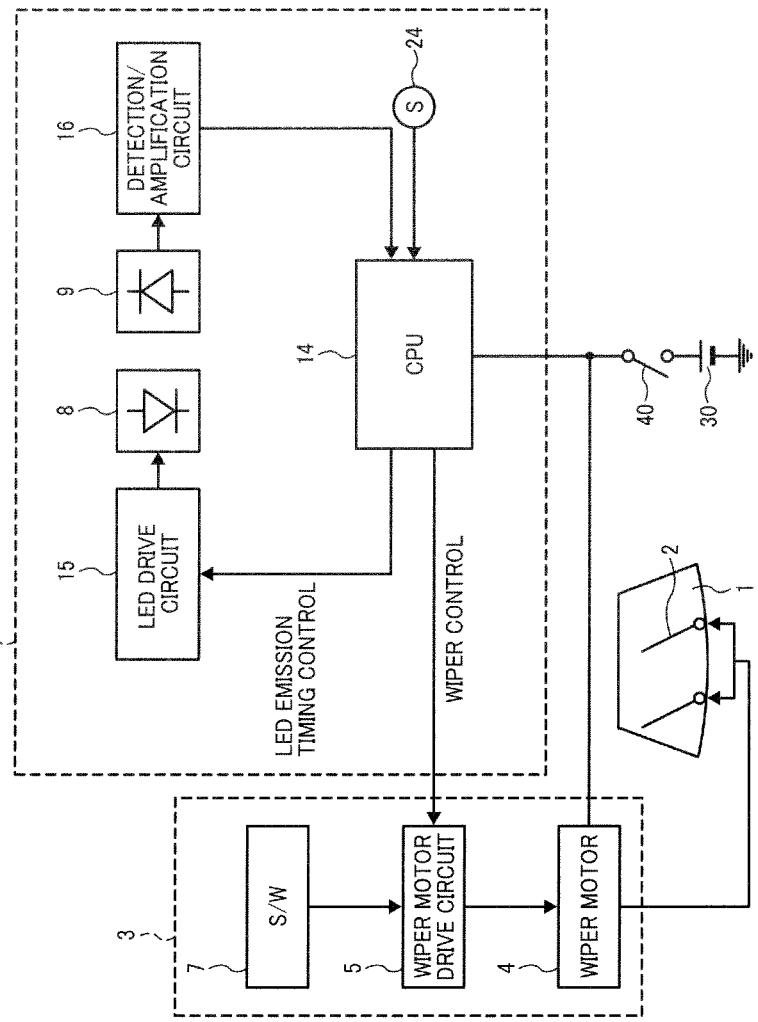
FIG. 41 is a block diagram of a vehicle equipped with an object detection apparatus according to another example embodiment.

FIG. 34 is a view of fogged windshield, and FIG. 41 is a view of frozen windshield. When the windshield 105 is fogged as illustrated in FIG. 34 or when the windshield 105 is frozen as illustrated in FIG. 35, the luminance variance for an image of the vehicle detection image area 231 becomes small.

Therefore, the luminance variance for the vehicle detection image area 231 can be effectively used to detect whether the windshield 105 is fogged or frozen.

Further, if the windshield 105 is fogged or frozen, an extraction of the edge portion of the hood becomes difficult.

Therefore, information whether the edge portion of the hood is extracted can be effectively used to detect whether the windshield 105 is fogged or frozen.

Then, as illustrated in FIG. 32, an exposure adjustment (e.g., exposure time adjustment) for the adhered object detection image area 232 is conducted in view of the light power of the light source unit 210 and spectrum properties of the light separation filter layer 251 of the optical filter 205 (S5).

Then, the image analyzer 102 obtains image data of the adhered object detection image area 232 (S6).

Then, the image analyzer 102 detects parameter for the wiper control and the defroster control using the image data of the adhered object detection image area 232 (S7), and stores the parameter to a given storage area (S8).

Figure 36:
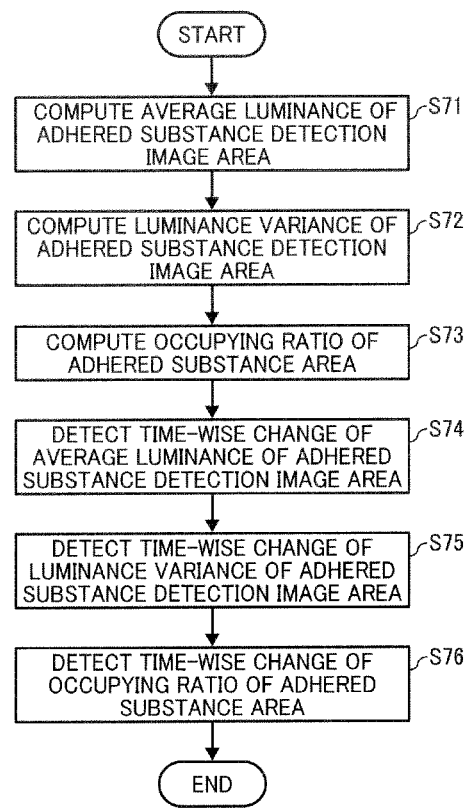
FIG. 36 is a flowchart showing the steps of a process of detecting parameter for wiper control and defroster control from the image data of the adhered object detection image area.

FIG. 36 is a flowchart showing the steps of a process of detecting parameter for the wiper control and the defroster control from the image data of the adhered object detection image area 232.

In the image analyzer 102, the average luminance value for the adhered object detection image area 232 is computed and used as a parameter for the wiper control and the defroster control (S71).

If the windshield 105 is adhered with raindrop, fogging or frozen portion, the average luminance value for the adhered object detection image area 232 decreases.

Therefore, it can detect whether the adhered object (e.g., raindrops, fogging, frozen) adheres based on the average luminance value of the adhered object detection image area 232.

Further, in the image analyzer 102, the luminance variance value for the adhered object detection image area 232 is computed and used as a parameter for the wiper control and the defroster control (S72).

If a size of raindrop is small (e.g., light rain), a total area of raindrop captured on the adhered object detection image area 232 becomes small, and the luminance variance value may not change so much compared to a case that the adhered object does not adhere on the windshield 105.

However, if raindrop having relatively greater size adhere on the windshield 105 with an increased number of raindrops, the luminance variance value becomes small because blurred images of raindrops are superimposed.

Further, when the windshield 105 is fogged or is frozen, the luminance variance value becomes also small.

Therefore, the image analyzer 102 can detect whether adhered object adhered on the windshield 105 is a level of light rain based on the luminance variance value for the adhered object detection image area 232.

Further, in the image analyzer 102, the occupying ratio of adhered object area on the adhered object detection image area 232 is computed and used as a parameter for detecting the wiper control and the defroster control (S73).

The adhered object area on the adhered object detection image area 232 is a ratio of the number of pixels (image area), having the average luminance value exceeding the control value, with respect to the total number of pixels (total area) of the adhered object detection image area 232.

Because the occupying ratio of adhered object area of fogging portion and frozen portion is typically large, based on the occupying ratio of adhered object area on the adhered object detection image area 232, the image analyzer 102*t* can detect whether adhered object adhered on the windshield 105 is fogging and frozen but not at level of light rain.

Further, in the image analyzer 102, time-wise change of the above described average luminance, luminance variance and the occupying ratio of adhered object area can be detected as the parameter for the wiper control and the defroster control (S74 to S76).

The time-wise change is an amount changed from image data of the adhered object detection image area 232 captured last time to image data of the adhered object detection image area 232 captured current time. The frozen or fogging cannot increase rapidly in a short period of time, but the splash (spray of water raised by other vehicles) adhering the windshield 105 can increase rapidly in a short period of time.

Therefore, based on the time-wise change of the average luminance for the adhered object detection image area 232, luminance variance for the adhered object detection image area 232, and the occupying ratio of adhered object area, it can detect whether adhered object adhered on the windshield 105 is splash.

As shown in FIG. 32, upon storing the detected parameter for the wiper control and the defroster control, the image analyzer 102 determines the condition of the windshield 105 (S9).

FIG. 37 is a flowchart showing the steps of a process of determining the condition of the windshield 105. FIGS. 38 and 39 are tables having determination criteria for determining the condition of the windshield 105.

In a process of determining the conditions of the windshield 105, initially, it is determined whether the exposure time for the vehicle detection image area 231, determined by the automatic exposure adjustment at step S1, is smaller than a threshold A, for example, 40 ms (S91).

If the exposure time becomes great such as greater than the threshold A, it can be determined that an image capturing area is at night with a little light quantity. Therefore, whether the exposure time is smaller than the threshold A, it can be recognized whether the image capturing area is during the day or at night.

If it is determined that the image capturing area is at night, the determination precision of the condition of the windshield 105 based on the parameter obtained from the image data of the vehicle detection image area 231 (e.g., luminance variance, edge extraction result of the hood) becomes low.

Therefore, if it is determined at night, the parameter obtained from the image data of the vehicle detection image area 231 (e.g., luminance variance, edge extraction result of the hood) is not used, but the parameter obtained from the adhered object detection image area 232 is used to determine the condition of the windshield 105 in the image analyzer 102.

If it is determined that the image capturing area is during the day at step S91, then it is determined whether the luminance variance of the vehicle detection image area 231 is greater than a threshold B (S92), and this determination result is stored to a given storage area. The threshold B can be set by experiments or the like for each exposure time, and prepared as a table. The threshold B is preferably determined and used depending on each exposure time.

Further, if it is determined that the image capturing area is during the day at step S91, it is determined whether the edge portion of the hood in the vehicle detection image area 231 is extracted (S93), and this determination result is stored to a given storage area.

The extraction of the edge portion of the hood can be conducted as follows. For example, an image area including the hood and background is captured, and then a differential image for the horizontal edge component of image is generated based on luminance change of adjacent pixels in the vertical direction of the image.

The generated differential image is compared with each differential image pattern of the horizontal edge component stored in advance, with which comparison result is obtained.

If it is determined that a pattern matching deviation for each detected area is a given threshold or less based on the comparison result, it is determined that the edge portion of the hood is detected. If the edge portion can be extracted, it can be determined that fogging, frozen, or splash does not occur to the windshield 105.

Then, it is determined for various parameters obtained from the adhered object detection image area 232. Specifically, it is determined whether the average luminance for the adhered object detection image area 232 is greater or smaller than a threshold C (S94), and this determination result is stored in a given storage area.

As described above, if raindrops adhere on the windshield 105, the average luminance becomes small. For example, if the luminance of the adhered object detection image area 232 has 1024 gradient, it is determined whether the average luminance is smaller than 900 (threshold C), removing noise component, is detected.

Further, it is determined whether the luminance variance for the adhered object detection image area 232 is greater or smaller than a threshold D (S95), and this determination result is stored in a given storage area.

For example, if the luminance of the adhered object detection image area 232 has 1024 gradient, it can be determined that the windshield 105 is fogged or frozen when the luminance variance is smaller than the threshold D such as 50.

Further, it is determined whether the time-wise change of the average luminance for the adhered object detection image area 232 is greater or smaller than a threshold E (S96), and this determination result is stored in a given storage area.

If the time-wise change of the average luminance is determined greater than the threshold E at S96, with which it can be determined that splash has occurred.

Further, it is determined whether the occupying ratio of adhered object area on the adhered object detection image area 232 is smaller than a threshold F such as one-fifth (S97), and this determination result is stored in a given storage area.

For example, under a condition that the light emitted from the light source unit 210 irradiates evenly, if an area having the average luminance is smaller than the threshold F, it can be determined that light rain adheres, and if an area having the average luminance is one-fifth (⅕) or more, it can be determined that an object other than light rain adheres.

Further, in the image analyzer 102, a detection result of the temperature sensor 111 can be used as a parameter for the wiper control and the defroster control, in which it is determined whether the ambient temperature detected by the temperature sensor 111 is greater or smaller than a threshold G (S98), and this determination result is stored in a given storage area.

For example, if the ambient temperature is zero degree (threshold G) or less, it can be determined that snowing or frozen occurs.

Upon obtaining the determination result for each of parameters, based on the determination result for each of parameters and information included in the table shown in FIGS. 38 and 39, the condition of the windshield 105 can be determined (S99).

In this condition determination, the determination result for each of parameters may be preferably set with weighting. For example, the parameter detected for the adhered object detection image area 232 and ambient temperature may be set with a weighting coefficient of 10, and the parameter detected for the vehicle detection image area 231 may be set with a weighting coefficient of 5.

Further, as for the determination result for each of parameters, 1 is set when a difference exists with a normal value, and 0 is set when a difference does not exist with a normal value.

Then, the determination result for each of parameters is multiplied with the weighting coefficient to obtain a total sum of the determination result the parameters. Then, the total sum is compared with a threshold. With this configuration, even if the determination result for each of parameters does not exactly match the information in the tables shown in FIGS. 38 and 39, the conditions of the windshield 105 can be determined.

Further, if it is determined that the parameter for the adhered object detection image area 232 is different from the normal value, the wiper may be operated one time, and then condition of the windshield 105 can be checked and determined again using each parameter.

As shown in FIG. 32, when the determination result for condition of the windshield 105 is obtained, the image analyzer 102 issues instructions for processes and controls such as wiper control and defroster control matched to the result of condition determination (S10).

FIG. 40 is an example of table for the wiper control and defroster control. The image analyzer 102 issues instructions for processes and controls at S10 in view of on a table shown in FIG. 40.

For example, the wiper control controls the wiper speed at three steps (e.g., slow, normal, fast), and the defroster control controls whether hot air is supplied to the inner face of the windshield 105 with a maximum wind volume.

(Object Detection Apparatus (2))

A description is given of an object detection apparatus according to another example embodiment of the present invention.

FIG. 41 is a block diagram of a vehicle equipped with an object detection apparatus 6 according to another example embodiment of the present invention. In this configuration, the object detection apparatus 6 is applied to an automatic wiper control apparatus for a vehicle.

A shown in FIG. 41, a vehicle includes, for example, a windshield 1, a wiper blade 2, a wiper control unit 3, and the object detection apparatus 6.

The windshield 1 is a member where raindrop may adhere, and can be made of, for example, soda-lime glass.

The wiper blade 2 is used to wipe or remove raindrop adhered on the windshield 1.

The wiper control unit 3 controls operation of the wiper blade 2. The wiper control unit 3 includes, for example, a wiper motor 4, a wiper motor drive circuit 5, and a wiper switch (S/W) 7. The wiper motor 4 is an electrical driver that drives the wiper blade 2. The wiper switch 7 is used as a switch to set start and stop of automatic control of the wiper blade 2.

The wiper switch 7 can be set to setting positions of, for example, five levels by a driver.

When the wiper switch 7 is set to an automatic control, a wiper wiping mode can be determined based on raindrop detection signal detected by the object detection apparatus 6, and a wiper control signal corresponding to the raindrop detection signal is output to the wiper motor drive circuit 5, with which the wiper blade 2 can be automatically controlled.

The object detection apparatus 6 includes, for example, a central processing unit (CPU) 14 used as a computing unit. The object detection apparatus 6 is supplied with power from a vehicle-installed power source 32 when an ignition switch 40 is turned ON and the wiper switch 7 is set to the automatic control.

Figure 42:
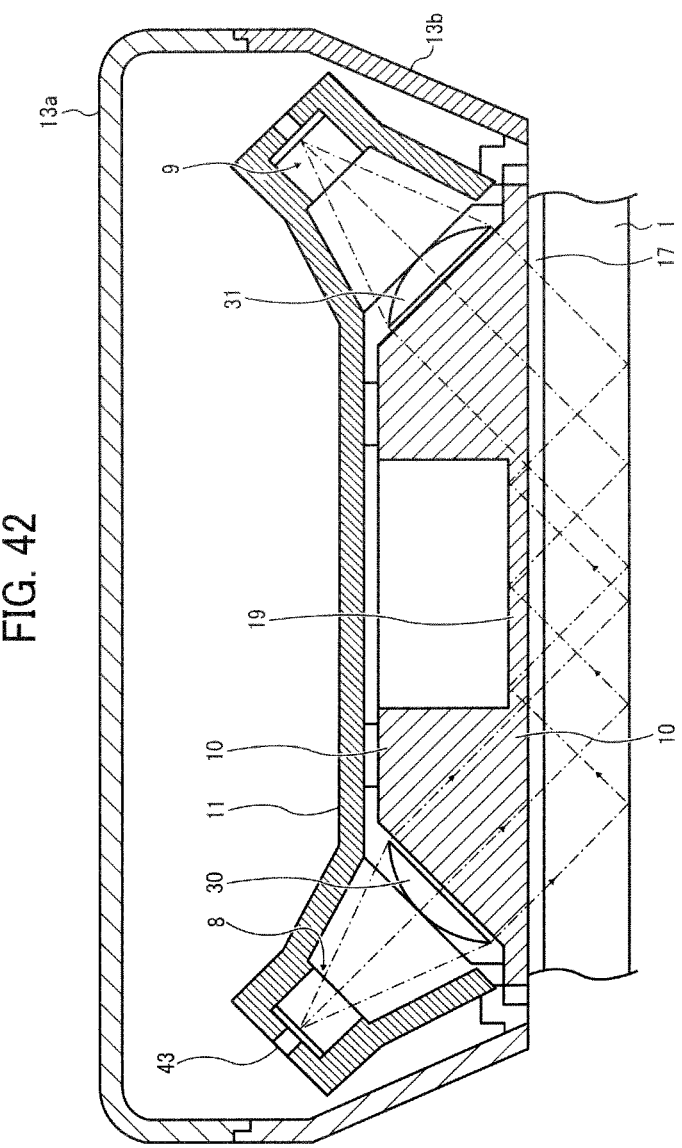
FIG. 42 is a cross-sectional view of a configuration of the object detection apparatus according to example embodiments.

FIG. 42 is a cross-sectional view of a configuration of the object detection apparatus 6. The object detection apparatus 6 is disposed at an inner face of the windshield 1 within a wiping area of the wiper blade 2.

As to the object detection apparatus 6, light from a light emitting element 8 such as a light emitting diode (hereinafter, LED 8) that emits infrared light is incident to the windshield 1, and then reflected by the windshield 1. The reflected light is received by a light receiving element 9 (hereinafter, photodiode 9).

As illustrated in FIG. 41, light emission timing of the LED 8 (i.e. power-ON and power-OFF timing from vehicle-installed power source 32) is controlled by the CPU 14 via a LED drive circuit 15.

Further, as illustrated in FIG. 41, an output value of the photodiode 9 is processed for photo-voltage conversion by a detection/amplification circuit 16, and is input to the CPU 14.

The object detection apparatus 6 is disposed with a prism 10 at an inner face side of the windshield 1, in which the prism 10 is used to configure a light path from the LED 8 to the light receiving element 9.

The prism 10 can be used as the light guide member according to an example embodiment of the present invention, and is disposed between the LED 8 and the windshield 1, and between the windshield 1 and the photodiode 9. The prism 10 is used to enter light from the LED 8 to the photodiode 9. Similar to the above described reflective deflection prism 220, the prism 10 has a convex face having curvature used as a contact face contactable to an attachment face of the windshield 1 having curvature.

Further, the prism 10 is made of, for example, resin such as norborn, but can be made of polycarbonate acryl.

The prism 10 is attached and contacted to the windshield 1 via an intervening member (e.g., adhesive sheet of silicone resin) that can pass infrared light. The prism 10 can be attached using the intervening member as similar to the reflective deflection prism 220 of the object detection apparatus 101.

Further, the prism 10 reflects reflection light from the windshield 1 to the photodiode 9 that receives the reflection light, and also blocks entering of the sunlight from the outside of the vehicle to the photodiode 9.

For example, when no raindrop adheres on the windshield 1, light from the LED 8 passes the prism 10 and totally reflects on an inner face of the windshield 1. Then, this totally reflected infrared light is totally reflected by the reflection portion 19 of the prism 10, and totally reflected on the inner face of the windshield 1, and then enters the photodiode 9.

In contrast, when raindrops adhere on the windshield 1, light from the LED 8 passing the prism 10 is not totally reflected on the inner face of the windshield 1, with which light quantity of light that enters the photodiode 9 from the LED 8 decreases.

As to the object detection apparatus 6, when raindrops adhere on the windshield 1, reflectance at the windshield 1 changes such as smaller reflectance. Based on decrease of light quantity received by the photodiode 9, an adhered object such as raindrop amount can be detected.

As to the object detection apparatus 6, a raindrop detection signal from the windshield 1 becomes different whether raindrop exists or not. Therefore, by monitoring change of raindrop detection signal, it can detect whether raindrop exists or not, and the wiper blade 2 can be automatically activated when raindrop exists.

A base unit 11 retains the LED 8 and the photodiode 9.

Further, the LED 8, the photodiode 9 and the base unit 11 are encased in cover casings 13a and 13b and integrated.

Such integrally formed object detection apparatus 6 is fixed on an inner face of the windshield 1 using an intervening member 17.

The prism 10 includes the reflection portion 19 at the center of the prism 10. As illustrated in FIG. 42, thickness of the reflection portion 19 is thin compared to other portions.

An aspherical lens 30 deflects light from the LED 8 to parallel light, and then the light passes the prism 10. The aspherical lens 30 can be integrally formed with the prism 10.

Further, an aspherical lens 31 deflects the light passing the prism 10 to parallel light, and then the light enters the photodiode 9. The aspherical lens 31 can be integrally formed with the prism 10.

As to the above described object detection apparatus 6, even if the object detection apparatus is attached to the windshield 1 having curvature, detection performance of the object detection apparatus 6 can be improved, in which detection performance of the object detection apparatus 6 can be secured at good enough level.

(Vehicle)

A description is given of vehicles according to example embodiments. A description is given of the vehicle 100 of FIG. 1 and the vehicle of FIG. 41 as example embodiments of the present invention.

As illustrated in FIG. 1, the vehicle 100 includes the object detection apparatus 101 near a rear view mirror disposed at an upper side and inner side of the windshield 105 in the vehicle 100.

Further, as illustrated in FIG. 41, the vehicle according to another example embodiment can include the object detection apparatus 6 near a rear view mirror disposed at an upper side and inner side of the windshield 105 in the vehicle 100.

As to the vehicles according to example embodiments, an attachment position of the object detection apparatus according to example embodiments is not limited to the above described position but can be other positions as long as an outside view of vehicle-forward or front direction can be detected.

As to the vehicles according to example embodiments, even if the object detection apparatus is attached to the windshield having curvature, the vehicle having improved detection performance of the object detection apparatus can be provided, in which detection performance of the object detection apparatus can be secured at good enough level.

As to the above described example embodiment, detection performance of an object detection apparatus can be improved.

Numerous additional modifications and variations are possible in light of the above teachings. It is therefore to be understood that, within the scope of the appended claims, the disclosure of the present invention may be practiced otherwise than as specifically described herein. For example, elements and/or features of different examples and illustrative embodiments may be combined each other and/or substituted for each other within the scope of this disclosure and appended claims.

What is claimed is:

1. A light guide member configured for an object detection apparatus, the object detection apparatus including a light source unit, and a detection unit for detecting an object adhered on a surface of a light translucent member of a vehicle based on change of light quantity of reflection light received from the light translucent member when light exiting from the light source unit is reflected from the light translucent member having a face having curvature, the light guide member comprising:

a detection face where the exiting light exits to a rear face of the light translucent member and the reflection light reflected from the light translucent member enters, the detection face including a detection area where a part of the reflection light to enter the detection unit passes through, and a non-detection area where remaining part of the reflection light not to enter the detection unit passes through;

a first intervening member disposed on the detection face, a part or entire of the detection area attachable to a rear face of the light translucent member via the first intervening member; and a second intervening member disposed on the detection face, a part or entire of the non-detection area attachable to the rear face of the light translucent member via the second intervening member, wherein the first intervening member has flexibility greater than flexibility of the second intervening member, and wherein curvature of the detection ace is smaller than curvature of the light translucent member facing the detection face.

2. The light guide member of claim 1, wherein height of the second intervening member is lower than height of the first intervening member.

3. The light guide member of claim 1, wherein at least a part of the detection area is attached to the rear face of the light translucent member via the first intervening member, and at least a part of the non-detection area is attached to the rear face of the light translucent member via the second intervening member.

4. The light guide member of claim 1, wherein the detection face includes an area where the reflection light passes, the area being the center of curvature.

5. The light guide member of claim 1, wherein the detection face has the curvature along a long side direction at an area of the detection face where the reflection light passes through.

6. The light guide member of claim 1, wherein the light source unit includes a plurality of light emitting points arranged in a direction corresponding to a vehicle width direction of the vehicle, and the detection face has curvature along a direction corresponding to the vehicle width direction.

7. The light guide member of claim 1, wherein the light translucent member is a windshield, and the object to adhere on a surface of the windshield is raindrop.

8. An object detection apparatus for detecting an object adhered on a surface of a light translucent member of a vehicle, comprising:

a light source unit;

the light guide member of claim 1 used for guiding light exiting from the light source unit to the light translucent member; and a detection unit to detect an object adhered on the surface of the light translucent member based on change of light quantity of reflection light received from the light translucent member when light enters the light translucent member via the light guide member, passes through the light translucent member, and then reflects on the surface of the light translucent member.

9. A vehicle comprising:

the object detection apparatus of claim 8 that detects an object adhered on a surface of the light translucent member of the vehicle.

10. A light guide member configured for an object detection apparatus, the object detection apparatus including a light source, and an object sensor for detecting an object adhered on a surface of a light translucent member constituting a part of a vehicle based on change of light quantity of reflection light received from the light translucent member when light exiting from the light source is reflected from the light translucent member having a face having curvature, the light guide member comprising:

- a detection face where the exiting light exits to a rear face of the light translucent member and the reflection light reflected from the light translucent member enters, the detection face including a detection area where a part of the reflection light to enter the object sensor passes through, and a non-detection area where remaining part of the reflection light not to enter the object sensor passes through;
- a first intervening member disposed on the detection face, a part or entire of the detection area attachable to a rear face of the light translucent member via the first intervening member; and
- a second intervening member disposed on the detection face, a part or entire of the non-detection area attachable to the rear face of the light translucent member via the second intervening member,
- wherein the first intervening member has flexibility greater than flexibility of the second intervening member, and
- wherein the detection face of the light guide member is configured to have curvature smaller than curvature of the light translucent member that (i) constitutes a part of the vehicle and (ii) faces said detection face of the light guide member.

11. The light guide member of claim 10, wherein height of the second intervening member is lower than height of the first intervening member.

12. The light guide member of claim 10, wherein at least a part of the detection area is attached to the rear face of the light translucent member via the first intervening member, and at least a part of the non-detection area is attached to the rear face of the light translucent member via the second intervening member.

13. The light guide member of claim 10, wherein the detection face includes an area where the reflection light passes, the area being the center of curvature.

14. The light guide member of claim 10, wherein the detection face has the curvature along a long side direction at an area of the detection face where the reflection light passes through.

15. The light guide member of claim 10, wherein the light source includes a plurality of light emitting points arranged in a direction corresponding to a vehicle width direction of the vehicle, and the detection face has curvature along a direction corresponding to the vehicle width direction.

16. The light guide member of claim 10, wherein the light translucent member is a windshield, and the object to adhere on a surface of the windshield is raindrop.

17. An object detection apparatus for detecting an object adhered on a surface of a light translucent member of a vehicle, comprising:

- the light source,
- the light guide member of claim 10 used for guiding light exiting from the light source to the light translucent member; and
- the object sensor to detect an object adhered on the surface of the light translucent member based on change of light quantity of reflection light received from the light translucent member when light enters the light translucent member via the light guide member, passes through the light translucent member, and then reflects on the surface of the light translucent member.

* * * * *